US009781925B2

United States Patent
Yamada et al.

(10) Patent No.: US 9,781,925 B2
(45) Date of Patent: *Oct. 10, 2017

(54) SYNTHETIC POLYMER FILM WHOSE SURFACE HAS MICROBICIDAL ACTIVITY, MULTILAYER STRUCTURE HAVING SYNTHETIC POLYMER FILM, STERILIZATION METHOD WITH THE USE OF SURFACE OF SYNTHETIC POLYMER FILM, METHOD FOR REACTIVATING SURFACE OF SYNTHETIC POLYMER FILM, MOLD FOR PRODUCTION OF SYNTHETIC POLYMER FILM, AND MOLD MANUFACTURING METHOD

(71) Applicant: Sharp Kabushiki Kaisha, Sakai, Osaka (JP)

(72) Inventors: Miho Yamada, Sakai (JP); Kiyoshi Minoura, Sakai (JP); Takahiro Nakahara, Sakai (JP); Seiji Takami, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/386,131

(22) Filed: Dec. 21, 2016

(65) Prior Publication Data
US 2017/0099835 A1 Apr. 13, 2017

Related U.S. Application Data

(62) Division of application No. 14/771,833, filed as application No. PCT/JP2015/056496 on Mar. 5, 2015.

(30) Foreign Application Priority Data

Apr. 22, 2014 (JP) ................................. 2014-088092
Jun. 13, 2014 (JP) ................................. 2014-122774
Dec. 24, 2014 (JP) ................................. 2014-261160

(51) Int. Cl.
*A01N 25/34* (2006.01)
*A01N 37/02* (2006.01)
(Continued)

(52) U.S. Cl.
CPC ............. *A01N 25/34* (2013.01); *A01N 37/02* (2013.01); *A01N 37/06* (2013.01); *A61L 9/00* (2013.01);
(Continued)

(58) Field of Classification Search
CPC ....................................................... A01N 25/34
See application file for complete search history.

(56) References Cited

U.S. PATENT DOCUMENTS

2003/0205475 A1 11/2003 Sawitowski
2007/0159698 A1 7/2007 Taguchi et al.
(Continued)

FOREIGN PATENT DOCUMENTS

CN    201329050 Y    10/2009
JP    H-024843       1/1996
(Continued)

OTHER PUBLICATIONS

Trafton. "MIT's anti-microbial 'paint' kills flu, bacteria". Nov. 30, 2006.*
(Continued)

*Primary Examiner* — Donald Spamer
(74) *Attorney, Agent, or Firm* — Harness, Dickey and Pierce, P.L.C.

(57) ABSTRACT

A synthetic polymer film (34A), (34B) having a surface which has a plurality of first raised portions (34Ap), (34Bp), wherein a two-dimensional size of the plurality of first raised portions (34Ap), (34Bp) is in a range of more than 20 nm and less than 500 nm when viewed in a normal direction of the synthetic polymer film (34A), (34B); and the surface has a microbicidal effect.

13 Claims, 20 Drawing Sheets

(51) Int. Cl.
*A61L 9/00* (2006.01)
*A01N 37/06* (2006.01)
*B08B 1/00* (2006.01)
*B08B 3/08* (2006.01)
*B08B 11/00* (2006.01)

(52) U.S. Cl.
CPC ............... *B08B 1/006* (2013.01); *B08B 3/08* (2013.01); *B08B 11/00* (2013.01)

(56) References Cited

U.S. PATENT DOCUMENTS

| | | |
|---|---|---|
| 2010/0203161 A1 | 8/2010 | Gehri et al. |
| 2011/0235181 A1 | 9/2011 | Hayashibe et al. |
| 2011/0281068 A1 | 11/2011 | David et al. |
| 2012/0318772 A1 | 12/2012 | Minoura et al. |
| 2013/0057958 A1 | 3/2013 | Minoura et al. |
| 2014/0077418 A1 | 3/2014 | Otani et al. |
| 2015/0140154 A1 | 5/2015 | Isurugi et al. |
| 2015/0168610 A1 | 6/2015 | Fukui et al. |
| 2015/0273755 A1 | 10/2015 | Yee et al. |
| 2016/0212989 A1* | 7/2016 | Juodkazis ............... C12N 1/066 |

FOREIGN PATENT DOCUMENTS

| | | |
|---|---|---|
| JP | 2005-055114 A | 3/2005 |
| JP | 2008-197217 A | 8/2008 |
| JP | 4265729 B2 | 5/2009 |
| JP | 2009-166502 A | 7/2009 |
| JP | 2010-000719 A | 1/2010 |
| JP | 2010079200 A | 4/2010 |
| JP | 2012078438 A | 4/2012 |
| JP | 2012-514239 A | 6/2012 |
| JP | 2013033287 A | 2/2013 |
| JP | 2013-078573 A | 5/2013 |
| JP | 2014-029391 A | 2/2014 |
| JP | 2014-066975 A | 4/2014 |
| JP | 2014-202955 A | 10/2014 |
| JP | 2015-024549 A | 2/2015 |
| WO | WO-2011/125486 A1 | 10/2011 |
| WO | WO-2011/148721 A1 | 12/2011 |
| WO | WO-2013/183576 A1 | 12/2013 |
| WO | WO-2013/191092 A1 | 12/2013 |
| WO | WO-2014/021376 A1 | 2/2014 |
| WO | WO-2014/171365 A1 | 10/2014 |

OTHER PUBLICATIONS

Good Housekeeping. "Do-It-All Cleaning Guide". Sep. 7, 2011.*
E. P. Ivanova, "Bactericidal activity of black silicon", Nature Communications, Published Nov. 26, 2013, 19pgs, Macmillan Publishers Limited.
International Search Report PCT/ISA/210 for International Application No. PCT/JP2015/057327 dated Jun. 3, 2015.
Epstein, A.K. et al., "Liquid-infused structured surfaces with exceptional anti-biofouling performance," PNAS, Aug. 14, 2012, vol. 109, No. 33.
Yao, C. et al., "Decreased bacteria density on nanostructured polyurethane," Society for Biomaterials, pp. 1823-1828, Jun. 29, 2013.
Ivanova, E. et al., "Natural Bactericidal Surfaces: Mechanical Rupture of Pseudomonas aeruginosa Cells by Cicada Wings," Small Journal, pp. 1-6, 2012.
Office Action dated Dec. 29, 2016 issued in U.S. Appl. No. 14/771,833.

* cited by examiner (a)

(b)

(a)

(b)

(c)

(a)

(b)

(a)

(c)

(b)

(d)

(a)

(b)

(c)

(d)

(e)

(f)

(a)

(b)

(c)

(a)

(b)

(a)

(b)

(c)

(a)

(b)

(c)

(d)

(a)

(b)

(c)

(a)

(b)

(c)

SYNTHETIC POLYMER FILM WHOSE SURFACE HAS MICROBICIDAL ACTIVITY, MULTILAYER STRUCTURE HAVING SYNTHETIC POLYMER FILM, STERILIZATION METHOD WITH THE USE OF SURFACE OF SYNTHETIC POLYMER FILM, METHOD FOR REACTIVATING SURFACE OF SYNTHETIC POLYMER FILM, MOLD FOR PRODUCTION OF SYNTHETIC POLYMER FILM, AND MOLD MANUFACTURING METHOD

CROSS-REFERENCE TO RELATED APPLICATIONS

This patent application is a divisional of U.S. National Phase patent application Ser. No. 14/771,833, filed 1 Sep. 2015, which claims priority to International Application No. PCT/JP2015/056496, filed on 5 Mar. 2015, which claims priority to Japanese Patent Application No. 2014-261160, filed on 24 Dec. 2014, and Japanese Patent Application No. 2014-122774, filed on 13 Jun. 2014, and Japanese Patent Application No. 2014-088092, filed on 22 Apr. 2014. The entire disclosures of each of the above recited applications are incorporated herein by reference.

TECHNICAL FIELD

The present invention relates to a synthetic polymer film whose surface has a microbicidal activity, a multilayer structure having the synthetic polymer film, a sterilization method with the use of the surface of the synthetic polymer film, a method for reactivating the surface of the synthetic polymer film, a mold for production of the synthetic polymer film, and a mold manufacturing method. In this specification, the "mold" includes molds that are for use in various processing methods (stamping and casting), and is sometimes referred to as a stamper. The "mold" can also be used for printing (including nanoimprinting).

BACKGROUND ART

Recently, it was reported that surficial nanostructures of black silicon, wings of cicadas and dragonflies have a bactericidal activity (Non-patent Document 1). For example, reportedly, black silicon has 500 nm high nanopillars, and the physical structure of the nanopillars produces a bactericidal activity. Wings of cicadas and dragonflies have 240 nm high nanopillars.

According to Non-patent Document 1, black silicon has the strongest bactericidal activity on Gram-negative bacteria, while wings of dragonflies have a weaker bactericidal activity, and wings of cicadas have a still weaker bactericidal activity. The static contact angle (hereinafter, sometimes simply referred to as "contact angle") of the black silicon surface with respect to water is 80°, while the contact angles of the surface of wings of dragonflies and cicadas with respect to water are 153° and 159°, respectively.

CITATION LIST

Patent Literature

Patent Document 1: Japanese Patent No. 4265729
Patent Document 2: Japanese Laid-Open Patent Publication No. 2009-166502
Patent Document 3: WO 2011/125486
Patent Document 4: WO 2013/183576

Non-Patent Literature

Non-patent Document 1: Ivanova, E. P. et al., "Bactericidal activity of black silicon", Nat. Commun. 4:2838 doi: 10.1038/ncomms3838 (2013).

SUMMARY OF INVENTION

Technical Problem

The mechanism of killing bacteria by nanopillars is not clear from the results described in Non-patent Document 1. It is also not clear whether the reason why black silicon has a stronger bactericidal activity than wings of dragonflies and cicadas resides in the difference in height or shape of nanopillars or the difference in surface free energy (which can be evaluated by the contact angle).

The bactericidal activity of black silicon is difficult to utilize because black silicon is poor in mass productivity, and is hard but brittle so that the shapability is poor.

The present invention was conceived for the purpose of solving the above problems. The major objects of the present invention include providing a synthetic polymer film whose surface has a microbicidal activity, a multilayer structure having the synthetic polymer film, a sterilization method with the use of the surface of the synthetic polymer film, a method for reactivating the surface of the synthetic polymer film, a mold for production of the synthetic polymer film, and a mold manufacturing method.

Solution to Problem

A synthetic polymer film according to an embodiment of the present invention is a synthetic polymer film including a surface which has a plurality of first raised portions, wherein a two-dimensional size of the plurality of first raised portions is in a range of more than 20 nm and less than 500 nm when viewed in a normal direction of the synthetic polymer film; and the surface has a microbicidal effect.

In one embodiment, a static contact angle of the surface with respect to hexadecane is not more than 51°.

In one embodiment, an adjoining distance of the plurality of first raised portions is more than 20 nm and not more than 1000 nm.

In one embodiment, a height of the plurality of first raised portions is not less than 50 nm and less than 500 nm. The height of the plurality of first raised portions may be not more than 150 nm.

In one embodiment, the plurality of first raised portions are capable of warping (or tilting) when coming in contact with a microorganism. The warp (tilt) of the plurality of first raised portions can be reset when the microorganism is removed.

In one embodiment, a normal to a lateral surface of the plurality of first raised portions forms an inclination angle with respect to a direction perpendicular to the normal direction of the synthetic polymer film, and the inclination angle varies continuously or discontinuously with respect to a distance from a tip end of the plurality of first raised portions in the normal direction of the synthetic polymer film.

In one embodiment, the synthetic polymer film further includes a plurality of second raised portions superimposedly formed over the plurality of first raised portions, wherein a two-dimensional size of the plurality of second raised portions is smaller than the two-dimensional size of the plurality of first raised portions and does not exceed 100 nm.

In one embodiment, the plurality of second raised portions include a generally conical portion.

In one embodiment, a height of the plurality of second raised portions is more than 20 nm and not more than 100 nm.

In one embodiment, the synthetic polymer film further includes a lubricant. The lubricant is a fluoric lubricant or silicone lubricant. The HLB (Hydrophile-Lipophile Balance) value of the lubricant is preferably less than 7, and more preferably less than 4.

In one embodiment, the surface of the synthetic polymer film is treated with a mold releasing agent. The mold releasing agent is a fluoric mold releasing agent or silicone mold releasing agent.

In one embodiment, the surface of the synthetic polymer film is treated with an oil. The oil is, for example, hexadecane or oleic acid.

A multilayer structure according to an embodiment of the present invention includes: any of the above-described synthetic polymer films; and a cover film whose surface is provided with an oil, wherein the cover film is arranged such that the oil provided to the surface of the cover film comes in contact with the plurality of first raised portions.

A method for sterilizing a gas or liquid according to an embodiment of the present invention includes bringing the gas or liquid into contact with the surface of any of the above-described synthetic polymer films.

A method for reactivating a surface of a synthetic polymer film according to an embodiment of the present invention includes the steps of: (a) providing any of the above-described synthetic polymer films, the synthetic polymer film having a microorganism adhering to the surface; and (b) removing the microorganism by wiping the surface with a cloth soaked with water or alcohol.

A mold according to an embodiment of the present invention includes a surface, the surface having a plurality of first recessed portions and a plurality of second recessed portions formed in the plurality of first recessed portions, wherein a two-dimensional size of the plurality of first recessed portions is in a range of more than 20 nm and less than 500 nm when viewed in a normal direction of the surface of the mold, and a two-dimensional size of the plurality of second recessed portions is smaller than the two-dimensional size of the plurality of first recessed portions and does not exceed 100 nm.

A mold manufacturing method according to an embodiment of the present invention is a method for manufacturing the above-described mold, including: (a) a step of providing an aluminum base or an aluminum film deposited on a support; (b) an anodization step of applying a voltage at a first level while a surface of the aluminum base or the aluminum film is kept in contact with an electrolytic solution, thereby forming a porous alumina layer which has first recessed portions; (c) after step (b), an etching step of bringing the porous alumina layer into contact with an etching solution, thereby enlarging the first recessed portions; and (d) after step (c), applying a voltage at a second level which is lower than the first level while the porous alumina layer is kept in contact with an electrolytic solution, thereby forming second recessed portions in the first recessed portions.

In one embodiment, the first level is higher than 40 V, and the second level is equal to or lower than 20 V.

In one embodiment, the electrolytic solution is an oxalic acid aqueous solution.

Advantageous Effects of Invention

According to an embodiment of the present invention, a synthetic polymer film whose surface has a microbicidal activity, a multilayer structure having the synthetic polymer film, a sterilization method with the use of the surface of the synthetic polymer film, a method for reactivating the surface of the synthetic polymer film, a mold for production of the synthetic polymer film, and a mold manufacturing method.

DESCRIPTION OF EMBODIMENTS

Hereinafter, a synthetic polymer film whose surface has a microbicidal effect, a multilayer structure having the synthetic polymer film, a sterilization method with the use of the surface of the synthetic polymer film, a method for reactivating the surface of the synthetic polymer film, a mold for production of the synthetic polymer film, and a mold manufacturing method according to embodiments of the present invention are described with reference to the drawings.

In this specification, the following terms are used.

"Sterilization" (or "microbicidal") means reducing the number of proliferative microorganisms contained in an object, such as solid or liquid, or a limited space, by an effective number.

"Microorganism" includes viruses, bacteria, and fungi.

"Antimicrobial" generally includes suppressing and preventing multiplication of microorganisms and includes suppressing dinginess and slime which are attributed to microorganisms.

The present applicant conceived a method for producing an antireflection film which has a moth-eye structure (antireflection surface) with the use of an anodized porous alumina layer. Using the anodized porous alumina layer enables manufacture of a mold which has an inverted moth-eye structure with high mass-productivity (e.g., Patent Documents 1 to 4). The entire disclosures of Patent Documents 1 to 4 are incorporated by reference in this specification. Note that antireflection films which are placed over the surface of liquid crystal television displays manufactured and sold until now by the present applicant are hydrophilic. This is for the purpose of facilitating wiping away of grease, such as fingerprint, adhered to the moth-eye structure. If the moth-eye structure is not hydrophilic, an aqueous washing solution cannot effectively enter the gap between raised portions of the moth-eye structure so that the grease cannot be wiped away.

The present inventors developed the above-described technology and arrived at the concept of a synthetic polymer film whose surface has a microbicidal effect.

The configuration of a synthetic polymer film according to an embodiment of the present invention is described with reference to FIGS. 1(a) and 1(b).

Figure 1:
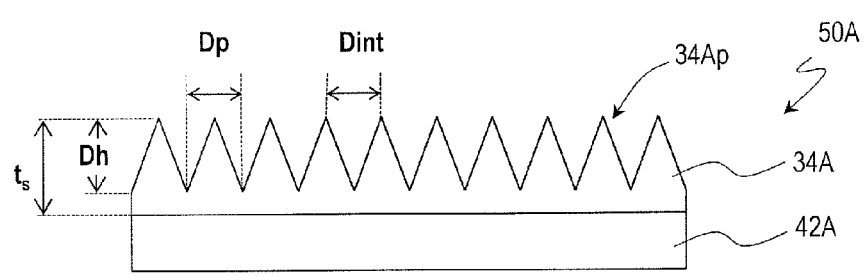
FIGS. 1 (a) and (b) are schematic cross-sectional views of synthetic polymer films 34A and 34B, respectively, according to embodiments of the present invention.
Figure 1:
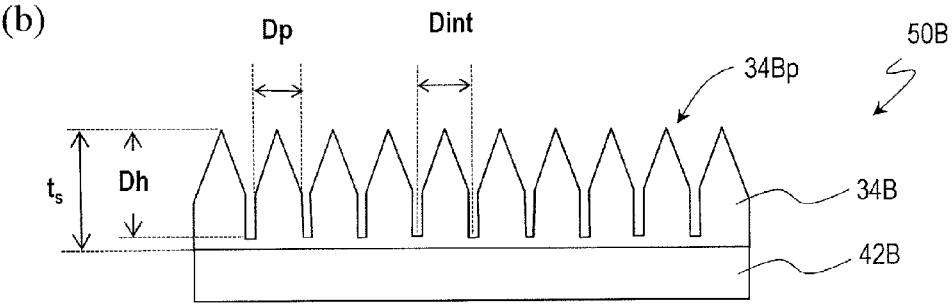

FIGS. 1(a) and 1(b) respectively show schematic cross-sectional views of synthetic polymer films 34A and 34B according to embodiments of the present invention. The synthetic polymer films 34A and 34B described herein as examples are formed on base films 42A and 42B, respectively, although the present invention is not limited to these examples. The synthetic polymer films 34A and 34B can be directly formed on a surface of an arbitrary object.

A film 50A shown in FIG. 1(a) includes a base film 42A and a synthetic polymer film 34A provided on the base film 42A. The synthetic polymer film 34A has a plurality of raised portions 34Ap over its surface. The plurality of raised portions 34Ap constitute a moth-eye structure. When viewed in a normal direction of the synthetic polymer film 34A, the two-dimensional size of the raised portions 34Ap, $D_p$, is in the range of more than 20 nm and less than 500 nm. Here, the "two-dimensional size" of the raised portions 34Ap refers to the diameter of a circle equivalent to the area of the raised portions 34Ap when viewed in a normal direction of the surface. When the raised portions 34Ap have a conical shape, for example, the two-dimensional size of the raised portions 34Ap is equivalent to the diameter of the base of the cone. The typical adjoining distance of the raised portions 34Ap, $D_{int}$, is more than 20 nm and not more than 1000 nm. When the raised portions 34Ap are densely arranged so that there is no gap between adjoining raised portions 34Ap (e.g., the bases of the cones partially overlap each other) as shown in FIG. 1(a), the two-dimensional size of the raised portions 34Ap, $D_p$, is equal to the adjoining distance $D_{int}$. The typical height of the raised portions 34Ap, $D_h$, is not less than 50 nm and less than 500 nm. As will be described later with experimental examples, a microbicidal activity is exhibited even when the height $D_h$ of the raised portions 34Ap is not more than 150 nm. The thickness of the synthetic polymer film 34A, $t_s$, is not particularly limited but only needs to be greater than the height $D_h$ of the raised portions 34Ap.

The surface of the synthetic polymer film 34A has a microbicidal ability. As will be described later with reference to FIGS. 5(a) to 5(d), the raised portions 34Ap break, for example, the cell walls of P. aeruginosa that is one of the Gram-negative bacteria, thereby killing P. aeruginosa bacteria.

The synthetic polymer film 34A shown in FIG. 1(a) has the same moth-eye structure as the antireflection films disclosed in Patent Documents 1 to 4. From the viewpoint of producing an antireflection function, it is preferred that the surface has no flat portion, and the raised portions 34Ap are densely arranged over the surface. Further, the raised portions 34Ap preferably has a such shape that the cross-sectional area (a cross section parallel to a plane which is orthogonal to an incoming light ray, e.g., a cross section parallel to the surface of the base film 42A) increases from the air side to the base film 42A side, e.g., a conical shape. From the viewpoint of suppressing interference of light, it is preferred that the raised portions 34Ap are arranged without regularity, preferably randomly. However, these features are unnecessary when only the microbicidal activity of the synthetic polymer film 34A is pursued. For example, the raised portions 34Ap do not need to be densely arranged. The raised portions 34Ap may be regularly arranged. Note that, however, the shape and arrangement of the raised portions 34Ap are preferably selected such that the raised portions 34Ap effectively act on microorganisms.

A film 50B shown in FIG. 1(b) includes a base film 42B and a synthetic polymer film 34B provided on the base film 42B. The synthetic polymer film 34B has a plurality of raised portions 34Bp over its surface. The plurality of raised portions 34Bp constitute a moth-eye structure. In the film 50B, the configuration of the raised portions 34Bp of the synthetic polymer film 34B is different from that of the raised portions 34Ap of the synthetic polymer film 34A of the film 50A. Descriptions of features which are common with those of the film 50A are sometimes omitted.

When viewed in a normal direction of the synthetic polymer film 34B, the two-dimensional size of the raised portions 34Bp, $D_p$, is in the range of more than 20 nm and less than 500 nm. The typical adjoining distance of the raised portions 34Bp, $D_{int}$, is more than 20 nm and not more than 1000 nm, and $D_p < D_{int}$ holds. That is, in the synthetic polymer film 34B, there is a flat portion between adjoining raised portions 34Bp. The raised portions 34Bp have the shape of a cylinder with a conical portion on the air side. The typical height of the raised portions 34Bp, $D_h$, is not less than 50 nm and less than 500 nm. The raised portions 34Bp may be arranged regularly or may be arranged irregularly. When the raised portions 34Bp are arranged regularly, $D_{int}$ also represents the period of the arrangement. This also applies to the synthetic polymer film 34A, as a matter of course.

In this specification, the "moth-eye structure" includes not only surficial nanostructures that have an excellent antireflection function and that are formed by raised portions which have such a shape that the cross-sectional area (a cross section parallel to the film surface) increases as do the raised portions 34Ap of the synthetic polymer film 34A shown in FIG. 1(a) but also surficial nanostructures that are formed by raised portions which have a part where the cross-sectional area (a cross section parallel to the film surface) is constant as do the raised portions 34Bp of the synthetic polymer film 34B shown in FIG. 1(b). Note that, from the viewpoint of breaking the cell walls and/or cell membranes of microorganisms, providing a conical portion is preferred. Note that, however, the tip end of the conical shape does not necessarily need to be a surficial nanostructure but may have a rounded portion (about 60 nm) which is generally equal to the nanopillars which form surficial nanostructures of the wings of cicadas.

The surfaces of the synthetic polymer films 34A and 34B may be treated when necessary. For example, a mold releasing agent or surface treatment agent may be applied to the surfaces in order to modify the surface tension (or surface free energy). Some types of the mold releasing agent or surface treatment agent lead to formation of a thin polymer film over the surfaces of the synthetic polymer films 34A and 34B. Alternatively, the surfaces of the synthetic polymer films 34A and 34B may be modified using plasma or the like. For example, by a plasma treatment using a gas which contains fluorine, lipophilicity can be given to the surfaces of the synthetic polymer films 34A and 34B. When the surfaces of the synthetic polymer films 34A and 34B have lipophilicity, the surfaces can have a relatively strong microbicidal activity.

The surface tension (or surface free energy) of the synthetic polymer films 34A and 34B can be modified not only by selecting a resin material itself which forms the synthetic polymer films 34A and 34B but also by adding a material which has a small HLB (Hydrophile-Lipophile Balance) value to a resin material. Further, both of these solutions may be used in combination. The HLB values of materials which are commonly commercially-available as lubricants are small. Particularly, a fluoric lubricant or silicone lubricant is preferably used. By adding a relatively small amount of the fluoric lubricant or silicone lubricant, a desired surface tension can be achieved. The HLB value of the lubricant is preferably less than 7, and more preferably less than 4. Some of the commercially-available lubricants (surfactants) have stated HLB values. The HLB value can be determined by the Davies' method or Kawakami method. The surface tension may be modified by adding the above-described mold releasing agent or surface treatment agent in combination with selection of a resin material which forms the synthetic polymer films 34A and 34B and addition of a lubricant, or solely by adding the above-described mold releasing agent or surface treatment agent.

As will be described later with experimental examples, the contact angle of the surface of the synthetic polymer film with respect to hexadecane is preferably not more than 51°. From the viewpoint of obtaining a synthetic polymer film which has such a surface, the synthetic polymer film preferably contains a fluoric compound. Example methods for obtaining a synthetic polymer film which contains a fluoric compound are described in the following paragraphs. In the examples described herein, a synthetic polymer film is formed using a UV-curable resin (e.g., an acrylic resin (including a methacrylic resin)). However, the same methods can also be utilized when any other photocurable or thermosetting resin is used.

FIRST METHOD: A fluorine-containing acrylic resin is obtained using a fluorine-containing monomer as an acrylic monomer (acrylate) which is a source material of an acrylic resin that forms the synthetic polymer film. The fluorine-containing acrylic resin may be formed by curing a fluorine-containing monomer (i.e., a monomer which contains fluorine in the molecule) or may be formed by curing a mixture of a fluorine-containing monomer and a monomer which does not contain fluorine in the molecule. Note that, in this specification, the monomer is merely a typical example of the source material of the photocurable resin, and it is not intended to exclude oligomers.

SECOND METHOD: A fluoric lubricant is added to the monomer that forms the synthetic polymer film. Here, the fluoric lubricant refers to a compound which would not react with the monomer, i.e., which does not directly or indirectly form a bond (covalent bond) to the skeleton of the resin and includes various fluoric lubricants which are commercially available as fluoric surfactants, fluoric lubricants, fluoric antifoaming agents, fluoric slipping agents, fluoric leveling agents, fluoric mold releasing agents, etc. These fluoric compounds typically have a structure in which hydrogen atoms in alkyl chains are replaced by fluorine atoms. The HLB value of the fluoric lubricant is preferably less than 7, and more preferably less than 4. The HLB value of a fluoric lubricant used in experimental examples which will be described later is less than 4.

THIRD METHOD: When employing a configuration which has an adhesive layer between the base film and the synthetic polymer film, a compound contained in the adhesive layer diffuses throughout the synthetic polymer film, and this phenomenon can be utilized. Such a phenomenon is disclosed in WO 2011/148721 of the present applicant. The entire disclosures of WO 2011/148721 are incorporated by reference in this specification. By adding the above-described fluoric lubricant to the adhesive layer, the same effects as those of the second method can be achieved.

The amount of the fluoric lubricant contained in the synthetic polymer film is preferably not less than 0.1 mass % and not more than 10 mass %, and more preferably not less than 0.5 mass % and not more than 5 mass %, with respect to the entire synthetic polymer film. If the amount of the fluoric lubricant is small, a sufficient effect is not achieved in some cases. If the amount of the fluoric lubricant is excessively large, sometimes it will produce a smear on the surface.

A mold for forming the moth-eye structure such as illustrated in FIGS. 1(a) and 1(b) over the surface (hereinafter, referred to as "moth-eye mold") has an inverted moth-eye structure obtained by inverting the moth-eye structure. Using an anodized porous alumina layer which has the inverted moth-eye structure as a mold without any modification enables inexpensive production of the moth-eye structure. Particularly when a moth-eye mold in the shape of a hollow cylinder is used, the moth-eye structure can be efficiently manufactured according to a roll-to-roll method. Such a moth-eye mold can be manufactured according to methods disclosed in Patent Documents 2 to 4.

A manufacturing method of a moth-eye mold 100A that is for production of the synthetic polymer film 34A is described with reference to FIGS. 2A(a) to 2A(e).

Figure 2A:
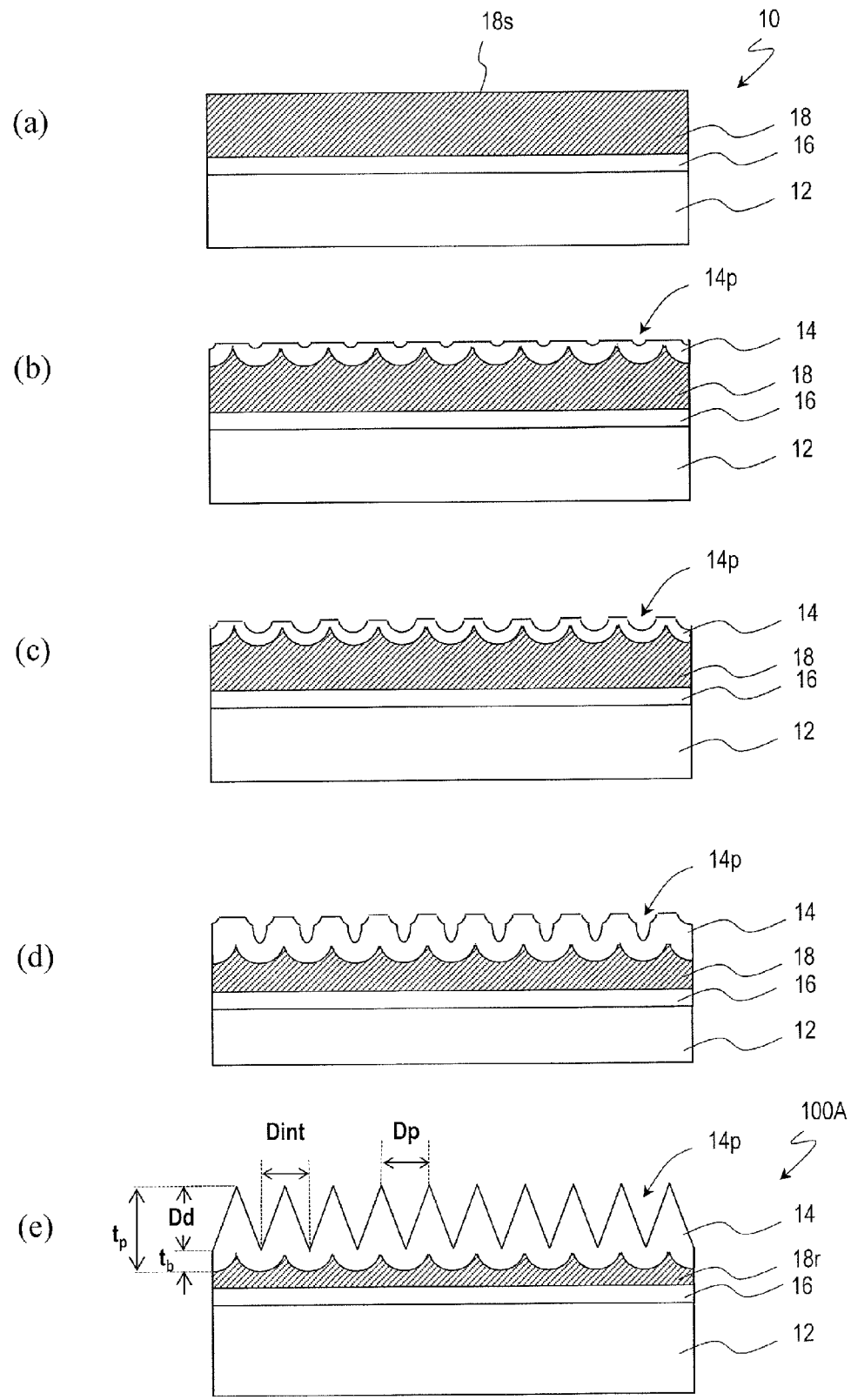
FIG. 2A (a) to (e) are diagrams for illustrating a method for manufacturing a moth-eye mold 100A and a configuration of the moth-eye mold 100A.

Firstly, a mold base 10 is provided which includes an aluminum base 12, an inorganic material layer 16 provided on a surface of the aluminum base 12, and an aluminum film 18 deposited on the inorganic material layer 16 as shown in FIG. 2A(a).

The aluminum base 12 used may be an aluminum base whose aluminum purity is not less than 99.50 mass % and less than 99.99 mass % and which has relatively high rigidity. The impurity contained in the aluminum base 12 may preferably include at least one element selected from the group consisting of iron (Fe), silicon (Si), copper (Cu), manganese (Mn), zinc (Zn), nickel (Ni), titanium (Ti), lead (Pb), tin (Sn) and magnesium (Mg). Particularly, Mg is preferred. Since the mechanism of formation of pits (hollows) in the etching step is a local cell reaction, the aluminum base 12 ideally does not contain any element which is nobler than aluminum. It is preferred that the aluminum base 12 used contains, as the impurity element, Mg (standard electrode potential: −2.36 V) which is a base metal. If the content of an element nobler than aluminum is 10 ppm or less, it can be said in terms of electrochemistry that the aluminum base 12 does not substantially contain the element. The Mg content is preferably 0.1 mass % or more of the whole. It is, more preferably, in the range of not more than about 3.0 mass %. If the Mg content is less than 0.1 mass %, sufficient rigidity cannot be obtained. On the other hand, as the Mg content increases, segregation of Mg is more likely to occur. Even if the segregation occurs near a surface over which a moth-eye mold is to be formed, it would not be detrimental in terms of electrochemistry but would be a cause of a defect because Mg forms an anodized film of a different form from that of aluminum. The content of the impurity element may be appropriately determined depending on the shape, thickness, and size of the aluminum base 12, in view of required rigidity. For example, when the aluminum base 12 in the form of a plate is prepared by rolling, the appropriate Mg content is about 3.0 mass %. When the aluminum base 12 having a three-dimensional structure of, for example, a hollow cylinder is prepared by extrusion, the Mg content is preferably 2.0 mass % or less. If the Mg content exceeds 2.0 mass %, the extrudability deteriorates in general.

The aluminum base 12 used may be an aluminum pipe in the shape of a hollow cylinder which is made of, for example, JIS A1050, an Al—Mg based alloy (e.g., JIS A5052), or an Al—Mg—Si based alloy (e.g., JIS A6063).

The surface of the aluminum base 12 is preferably a surface cut with a bit. If, for example, abrasive particles are remaining on the surface of the aluminum base 12, conduction will readily occur between the aluminum film 18 and the aluminum base 12 in a portion in which the abrasive particles are present. Not only in the portion in which the abrasive particles are remaining but also in a portion which has a roughened surface, conduction readily occurs between the aluminum film 18 and the aluminum base 12. When conduction occurs locally between the aluminum film 18 and the aluminum base 12, there is a probability that a local cell reaction will occur between an impurity in the aluminum base 12 and the aluminum film 18.

The material of the inorganic material layer 16 may be, for example, tantalum oxide ($Ta_2O_5$) or silicon dioxide ($SiO_2$). The inorganic material layer 16 can be formed by, for example, sputtering. When a tantalum oxide layer is used as the inorganic material layer 16, the thickness of the tantalum oxide layer is, for example, 200 nm.

The thickness of the inorganic material layer 16 is preferably not less than 100 nm and less than 500 nm. If the thickness of the inorganic material layer 16 is less than 100 nm, there is a probability that a defect (typically, a void; i.e., a gap between crystal grains) occurs in the aluminum film 18. If the thickness of the inorganic material layer 16 is not less than 500 nm, insulation is likely to occur between the aluminum base 12 and the aluminum film 18 due to the surface condition of the aluminum base 12. To realize anodization of the aluminum film 18 by supplying an electric current from the aluminum base 12 side to the aluminum film 18, the electric current needs to flow between the aluminum base 12 and the aluminum film 18. When employing a configuration where an electric current is supplied from the inside surface of the aluminum base 12 in the shape of a hollow cylinder, it is not necessary to provide an electrode to the aluminum film 18. Therefore, the aluminum film 18 can be anodized across the entire surface, while such a problem does not occur that supply of the electric current becomes more difficult as the anodization advances. Thus, the aluminum film 18 can be anodized uniformly across the entire surface.

To form a thick inorganic material layer 16, it is in general necessary to increase the film formation duration. When the film formation duration is increased, the surface temperature of the aluminum base 12 unnecessarily increases, and as a result, the film quality of the aluminum film 18 deteriorates, and a defect (typically, a void) occurs in some cases. When the thickness of the inorganic material layer 16 is less than 500 nm, occurrence of such a problem can be suppressed.

The aluminum film 18 is, for example, a film which is made of aluminum whose purity is not less than 99.99 mass % (hereinafter, sometimes referred to as "high-purity aluminum film") as disclosed in Patent Document 3. The aluminum film is formed by, for example, vacuum evaporation or sputtering. The thickness of the aluminum film 18 is preferably in the range of not less than about 500 nm and not more than about 1500 nm. For example, the thickness of the aluminum film 18 is about 1 μm.

The aluminum film 18 may be an aluminum alloy film disclosed in Patent Document 4 in substitution for the high-purity aluminum film. The aluminum alloy film disclosed in Patent Document 4 contains aluminum, a metal element other than aluminum, and nitrogen. In this specification, the "aluminum film" includes not only the high-purity aluminum film but also the aluminum alloy film disclosed in Patent Document 4.

Using the above-described aluminum alloy film enables to obtain a specular surface whose reflectance is not less than 80%. The average grain diameter of crystal grains that form the aluminum alloy film when viewed in the normal direction of the aluminum alloy film is, for example, not more than 100 nm, and that the maximum surface roughness Rmax of the aluminum alloy film is not more than 60 nm. The content of nitrogen in the aluminum alloy film is, for example, not less than 0.5 mass % and not more than 5.7 mass %. It is preferred that the absolute value of the difference between the standard electrode potential of the metal element other than aluminum which is contained in the aluminum alloy film and the standard electrode potential of aluminum is not more than 0.64 V, and that the content of the metal element in the aluminum alloy film is not less than 1.0 mass % and not more than 1.9 mass %. The metal element is, for example, Ti or Nd. The metal element is not limited to these examples but may be such a different metal element that the absolute value of the difference between the standard electrode potential of the metal element and the standard electrode potential of aluminum is not more than 0.64 V (for example, Mn, Mg, Zr, V, and Pb). Further, the metal element may be Mo, Nb, or Hf. The aluminum alloy film may contain two or more of these metal elements. The aluminum alloy film is formed by, for example, a DC magnetron sputtering method. The thickness of the aluminum alloy film is also preferably in the range of not less than about 500 nm and not more than about 1500 nm. For example, the thickness of the aluminum alloy film is about 1 μm.

Then, a surface 18s of the aluminum film 18 is anodized to form a porous alumina layer 14 which has a plurality of recessed portions (micropores) 14p as shown in FIG. 2A(b). The porous alumina layer 14 includes a porous layer which has the recessed portions 14p and a barrier layer (the base of the recessed portions (micropores) 14p). As known in the art, the interval between adjacent recessed portions 14p (the distance between the centers) is approximately twice the thickness of the barrier layer and is approximately proportional to the voltage that is applied during the anodization. This relationship also applies to the final porous alumina layer 14 shown in FIG. 2A(e).

The porous alumina layer 14 is formed by, for example, anodizing the surface 18s in an acidic electrolytic solution. The electrolytic solution used in the step of forming the porous alumina layer 14 is, for example, an aqueous solution which contains an acid selected from the group consisting of oxalic acid, tartaric acid, phosphoric acid, sulfuric acid, chromic acid, citric acid, and malic acid. For example, the surface 18s of the aluminum film 18 is anodized with an applied voltage of 80 V for 55 seconds using an oxalic acid aqueous solution (concentration: 0.3 mass %, solution temperature: 10° C.), whereby the porous alumina layer 14 is formed.

Then, the porous alumina layer 14 is brought into contact with an alumina etchant such that a predetermined amount is etched away, whereby the opening of the recessed portions 14p is enlarged as shown in FIG. 2A(c). By modifying the type and concentration of the etching solution and the etching duration, the etching amount (i.e., the size and depth of the recessed portions 14p) can be controlled. The etching solution used may be, for example, an aqueous solution of 10 mass % phosphoric acid, organic acid such as formic acid, acetic acid or citric acid, or sulfuric acid, or a chromate-phosphate mixture aqueous solution. For example, the etching is performed for 20 minutes using a phosphoric acid aqueous solution (10 mass %, 30° C.).

Then, the aluminum film 18 is again partially anodized such that the recessed portions 14p are grown in the depth direction and the thickness of the porous alumina layer 14 is increased as shown in FIG. 2A(d). Here, the growth of the recessed portions 14p starts at the bottoms of the previously-formed recessed portions 14p, and accordingly, the lateral surfaces of the recessed portions 14p have stepped shapes.

Thereafter, when necessary, the porous alumina layer 14 may be brought into contact with an alumina etchant to be further etched such that the pore diameter of the recessed portions 14p is further increased. The etching solution used in this step may preferably be the above-described etching solution. Practically, the same etching bath may be used.

In this way, by alternately repeating the anodization step and the etching step as described above through multiple cycles (e.g., 5 cycles: including 5 anodization cycles and 4 etching cycles), the moth-eye mold 100A that includes the porous alumina layer 14 which has the inverted moth-eye structure is obtained as shown in FIG. 2A(e). Since the process is ended with the anodization step, the recessed portions 14p have pointed bottom portion. That is, the resultant mold enables formation of raised portions with pointed tip ends.

The porous alumina layer 14 (thickness: $t_p$) shown in FIG. 2A(e) includes a porous layer (whose thickness is equivalent to the depth $D_d$ of the recessed portions 14p) and a barrier layer (thickness: $t_b$). Since the porous alumina layer 14 has a structure obtained by inverting the moth-eye structure of the synthetic polymer film 34A, corresponding parameters which define the dimensions may sometimes be designated by the same symbols.

The recessed portions 14p of the porous alumina layer 14 may have, for example, a conical shape and may have a stepped lateral surface. It is preferred that the two-dimensional size of the recessed portions 14p (the diameter of a circle equivalent to the area of the recessed portions 14p when viewed in a normal direction of the surface), $D_p$, is more than 20 nm and less than 500 nm, and the depth of the recessed portions 14p, $D_d$, is not less than 50 nm and less than 1000 nm (1 μm). It is also preferred that the bottom portion of the recessed portions 14p is acute (with the deepest part of the bottom portion being pointed). When the recessed portions 14p are in a densely packed arrangement, assuming that the shape of the recessed portions 14p when viewed in a normal direction of the porous alumina layer 14 is a circle, adjacent circles overlap each other, and a saddle portion is formed between adjacent ones of the recessed portions 14p. Note that, when the generally-conical recessed portions 14p adjoin one another so as to form saddle portions, the two-dimensional size of the recessed portions 14p, $D_p$, is equal to the adjoining distance $D_{int}$. The thickness of the porous alumina layer 14, $t_p$, is not more than about 1 μm.

Under the porous alumina layer 14 shown in FIG. 2A(e), there is an aluminum remnant layer 18r. The aluminum remnant layer 18r is part of the aluminum film 18 which has not been anodized. When necessary, the aluminum film 18 may be substantially thoroughly anodized such that the aluminum remnant layer 18r is not present. For example, when the inorganic material layer 16 has a small thickness, it is possible to readily supply an electric current from the aluminum base 12 side.

The manufacturing method of the moth-eye mold illustrated herein enables manufacture of a mold which is for production of antireflection films disclosed in Patent Documents 2 to 4. Since an antireflection film used in a high-definition display panel is required to have high uniformity, selection of the material of the aluminum base, specular working of the aluminum base, and control of the purity and components of the aluminum film are preferably carried out as described above. However, the above-described mold manufacturing method can be simplified because the microbicidal activity can be achieved without high uniformity. For example, the surface of the aluminum base may be directly anodized. Even if, in this case, pits are formed due to impurities contained in the aluminum base, only local structural irregularities occur in the moth-eye structure of the finally-obtained synthetic polymer film 34A, and it is estimated that there is little adverse influence on the microbicidal activity.

According to the above-described mold manufacturing method, a mold in which the regularity of the arrangement of the recessed portions is low, and which is suitable to production of an antireflection film, can be manufactured. In the case of utilizing the microbicidal ability of the moth-eye structure, it is estimated that the regularity of the arrangement of the raised portions does not exert an influence. A mold for formation of a moth-eye structure which has regularly-arranged raised portions can be manufactured, for example, as described in the following section.

For example, after formation of a porous alumina layer having a thickness of about 10 μm, the formed porous alumina layer is removed by etching, and then, anodization may be performed under the conditions for formation of the above-described porous alumina layer. A 10 μm thick porous alumina layer is realized by extending the anodization duration. When such a relatively thick porous alumina layer is formed and then this porous alumina layer is removed, a porous alumina layer having regularly-arranged recessed portions can be formed without being influenced by irregularities which are attributed to grains that are present at the surface of an aluminum film or aluminum base or the process strain. Note that, in removal of the porous alumina layer, using a mixture solution of a chromate and a phosphate is preferred. Although continuing the etching for a long period of time sometimes causes galvanic corrosion, the mixture solution of a chromate and a phosphate has the effect of suppressing galvanic corrosion.

A moth-eye mold for production of the synthetic polymer film 34B shown in FIG. 1(b) can be, basically, manufactured by combination of the above-described anodization step and etching step. A manufacturing method of a moth-eye mold 100B that is for production of the synthetic polymer film 34B is described with reference to FIGS. 2B(a) to 2B(c).

Firstly, in the same way as illustrated with reference to FIGS. 2A(a) and 2A(b), the mold base 10 is provided, and the surface 18s of the aluminum film 18 is anodized, whereby a porous alumina layer 14 which has a plurality of recessed portions (micropores) 14p is formed.

Figure 2B:
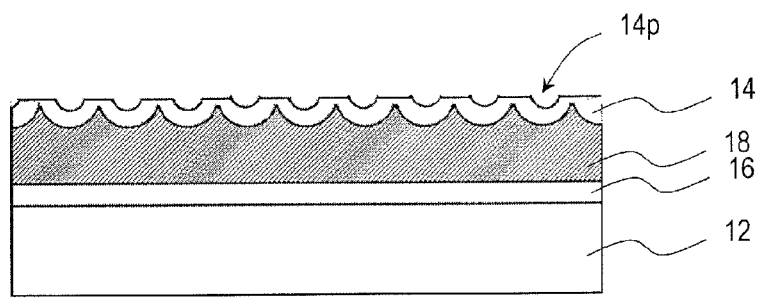
FIG. 2B (a) to (c) are diagrams for illustrating a method for manufacturing a moth-eye mold 100B and a configuration of the moth-eye mold 100B.
Figure 2B:
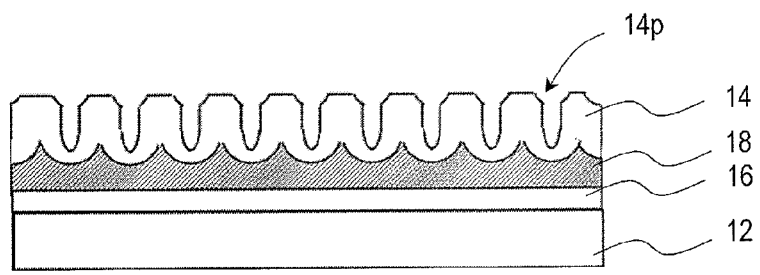
Figure 2B:
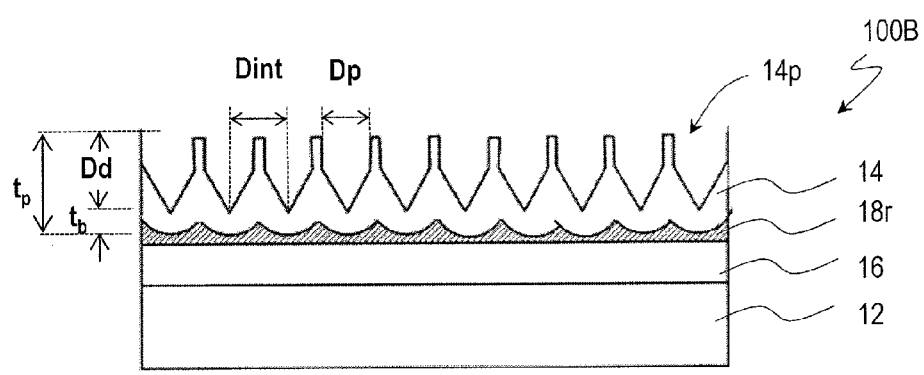

Then, the porous alumina layer 14 is brought into contact with an alumina etchant such that a predetermined amount is etched away, whereby the opening of the recessed portions 14p is enlarged as shown in FIG. 2B(a). In this step, the etched amount is smaller than in the etching step illustrated with reference to FIG. 2A(c). That is, the size of the opening of the recessed portions 14p is decreased. For example, the etching is performed for 10 minutes using a phosphoric acid aqueous solution (10 mass %, 30° C.)

Then, the aluminum film 18 is again partially anodized such that the recessed portions 14p are grown in the depth direction and the thickness of the porous alumina layer 14 is increased as shown in FIG. 2B(b). In this step, the recessed portions 14p are grown deeper than in the anodization step illustrated with reference to FIG. 2A(d). For example, the anodization is carried out with an applied voltage of 80 V for 165 seconds (in FIG. 2A(d), 55 seconds) using an oxalic acid aqueous solution (concentration: 0.3 mass %, solution temperature: 10° C.).

Thereafter, the etching step and the anodization step are alternately repeated through multiple cycles in the same way as illustrated with reference to FIG. 2A(e). For example, 3 cycles of the etching step and 3 cycles of the anodization step are alternately repeated, whereby the moth-eye mold 100B including the porous alumina layer 14 which has the inverted moth-eye structure is obtained as shown in FIG. 2B(c). In this step, the two-dimensional size of the recessed portions 14p, $D_p$, is smaller than the adjoining distance $D_{int}$ ($D_p < D_{int}$).

Figure 3:
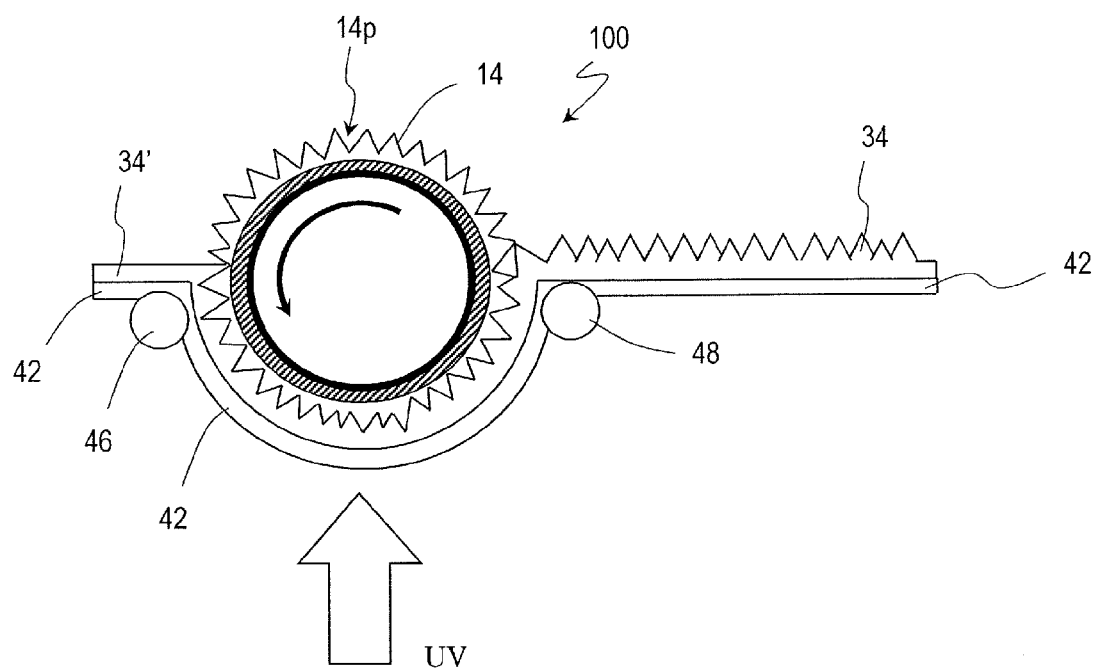
FIG. 3 A diagram for illustrating a method for producing a synthetic polymer film with the use of the moth-eye mold 100.

Next, a method for producing a synthetic polymer film with the use of a moth-eye mold 100 is described with reference to FIG. 3. FIG. 3 is a schematic cross-sectional view for illustrating a method for producing a synthetic polymer film according to a roll-to-roll method.

First, a moth-eye mold 100 in the shape of a hollow cylinder is provided. Note that the moth-eye mold 100 in the shape of a hollow cylinder is manufactured according to, for example, the manufacturing method described with reference to FIG. 2A.

As shown in FIG. 3, a base film 42 over which a UV-curable resin 34' is applied on its surface is maintained pressed against the moth-eye mold 100, and the UV-curable resin 34' is irradiated with ultraviolet (UV) light such that the UV-curable resin 34' is cured. The UV-curable resin 34' used may be, for example, an acrylic resin. The base film 42 may be, for example, a PET (polyethylene terephthalate) film or TAC (triacetyl cellulose) film. The base film 42 is fed from an unshown feeder roller, and thereafter, the UV-curable resin 34' is applied over the surface of the base film 42 using, for example, a slit coater or the like. The base film 42 is supported by supporting rollers 46 and 48 as shown in FIG. 3. The supporting rollers 46 and 48 have rotation mechanisms for carrying the base film 42. The moth-eye mold 100 in the shape of a hollow cylinder is rotated at a rotation speed corresponding to the carrying speed of the base film 42 in a direction indicated by the arrow in FIG. 3.

Thereafter, the moth-eye mold 100 is separated from the base film 42, whereby a synthetic polymer film 34 to which the inverted moth-eye structure of the moth-eye mold 100 is transferred is formed on the surface of the base film 42. The base film 42 which has the synthetic polymer film 34 formed on the surface is wound up by an unshown winding roller.

The surface of the synthetic polymer film 34 has the moth-eye structure obtained by inverting the surficial nanostructures of the moth-eye mold 100. According to the surficial nanostructure of the moth-eye mold 100 used, the synthetic polymer films 34A and 34B shown in FIGS. 1(a) and 1(b), respectively, can be produced. The material that forms the synthetic polymer film 34 is not limited to the UV-curable resin but may be a photocurable resin which is curable by visible light or may be a thermosetting resin.

Hereinafter, it is explained with experimental examples that the synthetic polymer film which has the above-described moth-eye structure over its surface has the microbicidal ability.

A mold manufactured according to the above-described mold manufacturing method was used to produce a synthetic polymer film having conical raised portions such as the raised portions 34Ap of the film 50A shown in FIG. 1(a). In sample films subjected to evaluation of the microbicidal activity, $D_p$ was about 200 nm, $D_{int}$ was about 200 nm, and $D_h$ was about 150 nm (see FIG. 5, for example). From the viewpoint of causing local deformation of the cell wall, it is preferred that there is a large distance between adjoining raised portions. The difference between $D_p$ and $D_{int}$ is preferably, for example, 0 times to twice $D_p$, and more preferably 0.5 times to twice $D_p$. Here, $D_p$, $D_{int}$, and $D_h$ represent the average values determined from SEM images. In photographing of the SEM images, a field emission scanning electron microscope (S-4700 manufactured by Hitachi, Ltd.) was used.

The resin material used for formation of the synthetic polymer film was a UV-curable resin. Sample film No. 1 and sample film No. 2 were produced using the same fluorine-containing acrylic resin. In sample film No. 2, a mold releasing agent was applied over the surface of the resultant synthetic polymer film, whereby a synthetic polymer film was obtained which had a different surface free energy from the surface of the synthetic polymer film of sample film No. 1. Sample film No. 3 was produced using a urethane acrylate-containing acrylic resin to which a fluorine-containing anionic lubricant F1 was added. The fluorine-containing anionic lubricant F1 used was FUTARGENT 150 (manufactured by NEOS Company Limited) commercially available as a fluoric slipping agent (or fluoric surfactant). The percentage of the added lubricant F1 to the total acrylic resin composition was 2 mass %. Sample film No. 4 was a synthetic polymer film which was produced using a urethane acrylate-containing acrylic resin (to which the above-described lubricant F1 was not added), the synthetic polymer film having a surface to which a mold releasing agent was applied. The mold releasing treatment for the synthetic polymer films of sample films No. 2 and No. 4 was spraying a fluoric mold releasing agent (OPTOOL DSX manufactured by DAIKIN INDUSTRIES, LTD) over the entire surface of the synthetic polymer films and drying the surface at room temperature in air. The mold releasing agent R1 used for sample film No. 2 and the mold releasing agent R2 used for sample film No. 4 were obtained by diluting OPTOOL DSX with perfluorohexane so as to have respective concentrations.

The surface tension of the sample films was evaluated by measuring the contact angle of water and hexadecane at 22° C. with respect to the sample films using a contact angle meter (PCA-1 manufactured by Kyowa Interface Science Co., Ltd). The average value of five measurements of the contact angle is shown in Table 1.

TABLE 1

| No. | SYNTHETIC POLYMER FILM (BASE FILM: PET) | CONTACT ANGLE OF WATER (°) | CONTACT ANGLE OF HEXADECANE (°) | MICROBICIDAL ABILITY |
| --- | --- | --- | --- | --- |
| 1 | FLUORINE-CONTAINING ACRYLIC RESIN A | 131.2 | 30.7 | ○ |
| 2 | FLUORINE-CONTAINING ACRYLIC RESIN A + MOLD RELEASING AGENT R1 (0.1 mass %) | 126.2 | 50.9 | Δ |
| 3 | URETHANE ACRYLATE-CONTAINING ACRYLIC RESIN B WITH FLUORIC LUBRICANT F1 ADDED | 12.0 | 4.8 | ○ |
| 4 | URETHANE ACRYLATE-CONTAINING ACRYLIC RESIN B + MOLD RELEASING AGENT R2 (0.01 mass %) | 73.3 | 9.4 | ○ |

The microbicidal ability was evaluated through the following procedure:

1. Beads with frozen *P. aeruginosa* bacteria (purchased from National Institute of Technology and Evaluation) were immersed in a broth at 37° C. for 24 hours, whereby the *P. aeruginosa* bacteria were thawed;
2. Centrifugation (3000 rpm, 10 minutes);
3. The supernatant of the broth was removed;
4. Sterilized water was added, and the resultant solution was stirred and thereafter subjected to centrifugation again;
5. Steps 2 to 4 were repeated three times to obtain an undiluted bacterial solution (bacteria count: 1E+08 CFU/mL);
6. 1/500 NB culture medium and bacterial dilution A (bacteria count: 1E+06 CFU/mL) were prepared.

1/500 NB culture medium: NB culture medium (nutrient broth medium E-MC35 manufactured by Eiken Chemical Co., Ltd.) was diluted 500-fold with sterilized water.

Bacterial Dilution A: Undiluted Bacterial Solution 500 μL+Broth 100 μL+Sterilized Water 49.4 mL;

7. Bacterial dilution B was prepared by adding the 1/500 NB culture medium as a nutrient source to bacterial dilution A (in accordance with JIS 22801 5.4a))
8. Bacterial dilution B was sprayed twice from a distance of about 10 cm on each of the sample films placed on a black acrylic plate (the amount of one spray: about 150 μL);
9. The sample films sprayed with bacterial dilution B are left in an airtight resin container (37° C., relative humidity 100%) for a predetermined time period;
10. Thereafter, the surfaces of the sample films were stamped with PETAN CHECK™ (product name: PT1025, manufactured by Eiken Chemical Co., Ltd.) such that the bacteria on the sample film surfaces were transferred to the standard agar medium;
11. The bacteria transferred to the standard agar medium were cultured at 37° C. for 24 hours, and thereafter, the presence/absence of colonies was checked.

Figure 4:
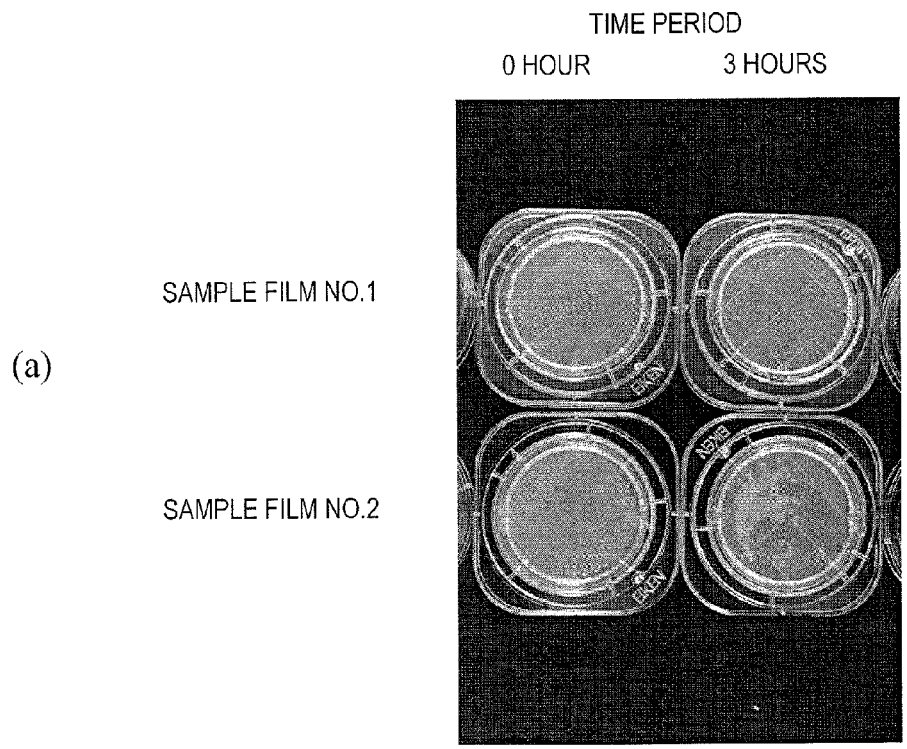
FIGS. 4 (a) and (b) are pictures for illustrating the evaluation results of the microbicidal ability of sample films No. 1 to No. 4 and are, specifically, optical images of the surfaces of agar media on which Pseudomonas aeruginosa (or "P. aeruginosa") bacteria were cultured. The upper part of (a) shows the evaluation results of sample film No. 1 (the time period that the sample film was left: 0 hour (5 minutes), 3 hours). The lower part of (a) shows the evaluation results of sample film No. 2 (the time period: 0 hour (5 minutes), 3 hours). The upper part of (b) shows the evaluation results of sample film No. 3 (the time period: 0 hour (5 minutes), 3 hours). The lower part of (b) shows the evaluation results of sample film No. 4 (the time period: 0 hour (5 minutes), 3 hours).
Figure 4:
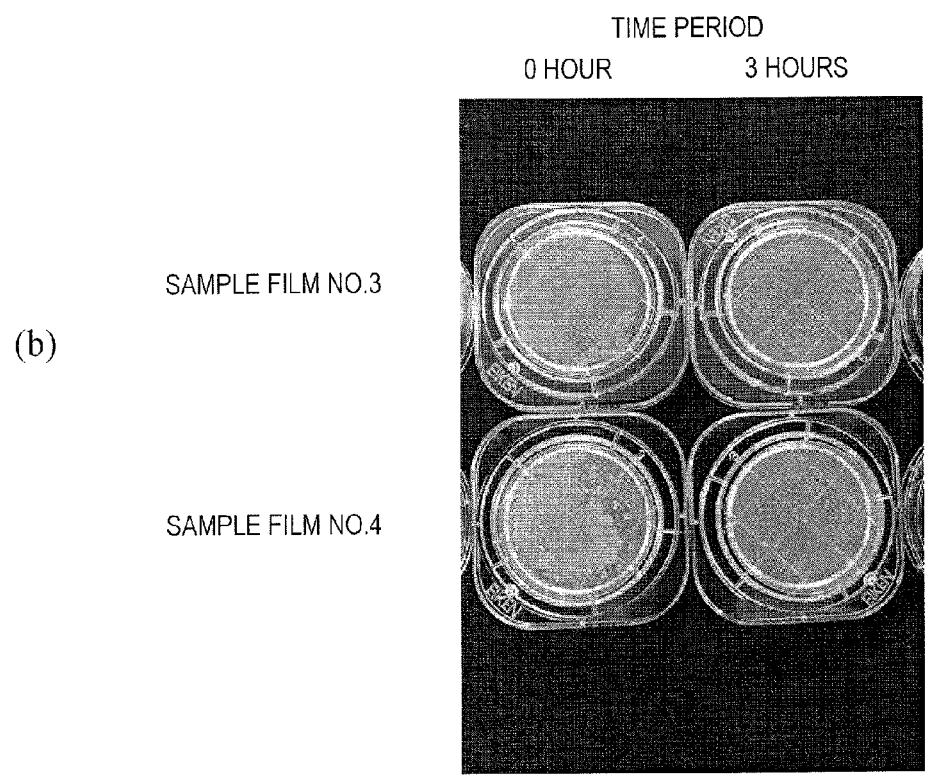

In each of sample films No. 1 to No. 4, films left at Step 9 under the conditions that the time period was 0 hour (5 minutes) or 3 hours were subjected to PETAN CHECK™ The results of culturing at the standard agar medium are shown in FIGS. 4(a) and 4(b). In FIG. 4(a), the upper part shows the evaluation results of sample film No. 1 (the time period: 0 hour (5 minutes), 3 hours), and the lower part shows the evaluation results of sample film No. 2 (the time period: 0 hour (5 minutes), 3 hours). In FIG. 4(b), the upper part shows the evaluation results of sample film No. 3 (the time period: 0 hour (5 minutes), 3 hours), and the lower part shows the evaluation results of sample film No. 4 (the time period: 0 hour (5 minutes), 3 hours).

Refer to FIGS. 4(a) and 4(b). As for sample films No. 1 to No. 4, the samples on the left hand side (the time period was 0 hour (5 minutes)) show that grown bacteria covers the substantially entire surface of the medium, while in the samples on the right hand side of sample films Nos. 1, 3 and 4 (the time period was 3 hours), growth of the bacteria was not detected. In the sample on the right hand side of sample film No. 2 (the time period: 3 hours), growth of the bacteria was detected, but the number of grown bacteria was obviously smaller than in the sample on the left hand side (the time period: 0 hour (5 minutes)).

From the foregoing, it is understood that every one of sample films No. 1 to No. 4 has a microbicidal activity. One of the possible reasons that the microbicidal activity of sample film No. 2 is weaker than that of sample film No. 1 is the difference in surface free energy. As seen from Table 1, the contact angle of sample film No. 2 with respect to hexadecane is 50.9°, which is greater by about 20° than that of sample film No. 1 (30.7°). That is, it is inferred that the microbicidal ability of sample film No. 2 is weaker because the surface of sample film No. 2 has inferior lipophilicity to the surface of sample film No. 1.

FIGS. 5(a) to 5(d) show examples of SEM (Scanning Electron Microscope) observation of *P. aeruginosa* bacteria which died at a surface of sample film No. 1 which had a moth-eye structure. The full scale in the SEM images of FIGS. 5(a) and 5(b) is 1 µm. FIGS. 5(c) and 5(d) are enlarged views of FIGS. 5(a) and 5(b), respectively, in which the full scale in the SEM images is 500 nm.

As seen from these SEM images, the tip end portions of the raised portions enter the cell wall (exine) of a *P. aeruginosa* bacterium. In FIGS. 5(c) and 5(d), the raised portions do not appear to break through the cell wall but appears to be taken into the cell wall. This might be explained by the mechanism suggested in the "Supplemental Information" section of Non-patent Document 1. That is, it is estimated that the exine (lipid bilayer) of the Gram-negative bacteria came close to the raised portions and deformed so that the lipid bilayer locally underwent a transition like a first-order phase transition (spontaneous reorientation) and openings were formed in portions close to the raised portions, and the raised portions entered these openings.

Apart from the validity of the above-described mechanism, it is inferred from the above-described experimental results that when the surface of a synthetic polymer film has appropriate lipophilicity (preferably, the contact angle with respect to hexadecane is not more than) 50.9°, the Gram-negative bacteria in the aqueous solution come close to the raised portions of the synthetic polymer film to cause interaction, and as a result, the raised portions enter the exine (lipid bilayer) of the Gram-negative bacteria so that the cell wall is broken. In this case, the force which acts on the exine of the Gram-negative bacteria depends on the free energy of the surface of the exine, the free energy of the surface of the raised portions, and the free energy of water which is in contact with these surfaces. It is estimated that, when the raised portions are lipophilic, the force which acts on the exine is large. As seen from the results of Table 1, the contact angle of the surface of the synthetic polymer film with respect to hexadecane is preferably not more than 51°, and more preferably not more than 31°. It can be said that, as the contact angle decreases, the microbicidal activity increases. Also as seen from the results of Table 1, the contact angle of the surface of the synthetic polymer film with respect to water ranges from 12.0° to 131.2°. It is understood that the hydrophilicity (or, conversely, hydrophobicity) of the surface of the synthetic polymer film which is evaluated by the contact angle of water does not directly relate to the microbicidal activity.

Next, the results of experiments for verifying the microbicidal activity achieved by the moth-eye structure of sample film No. 1 are described with reference to FIGS. 6(a) to 6(f). For comparison with sample film No. 1 that is a synthetic polymer film which has the moth-eye structure, a flat synthetic polymer film without the moth-eye structure which was made of the same resin material as sample film No. 1 (comparative example 1) and a PET film which is on the rear surface of sample film No. 1 (comparative example 2) were evaluated as to the microbicidal ability through the following procedure.

1. A 400 µL drop of the above-described bacterial dilution A (bacteria count: 1E+06 CFU/mL) was placed on each of the sample films. A cover (e.g., cover glass) was placed over the bacterial dilution A to adjust the amount of the bacterial dilution A per unit area (about 0.4 mL/cm²).

Meanwhile, a sample without a cover over the bacterial dilution A was also prepared.

2. The samples were left in an environment where the temperature was 37° C. and the relative humidity was 100% for a predetermined time period. Thereafter, the entire sample film with the bacterial dilution A and 10 mL sterilized water were put into a filter bag.

3. The sample films were rubbed with hands over the filter bag to sufficiently wash away the bacteria from the sample films (post-wash solution (sometimes referred to as "bacterial dilution B"), bacteria count: 1E+04 CFU/mL).

4. 1 mL of the post-wash solution was put into 9 mL phosphate buffer solution, whereby bacterial dilution C (bacteria count: 1E+03 CFU/mL) was prepared.

5. 1 mL of the bacterial dilution C was put into 9 mL phosphate buffer solution, whereby bacterial dilution D (bacteria count: 1E+02 CFU/mL) was prepared. Then, 1 mL of the bacterial dilution D was put into 9 mL phosphate buffer solution, whereby bacterial dilution E (bacteria count: 1E+01 CFU/mL) was prepared.

6. 1 mL drops of the bacterial dilutions C to E were placed on Petrifilm™ media (product name: Aerobic Count Plate (AC), manufactured by 3M). The bacteria were cultured at 37° C. with the relative humidity of 100%. After 48 hours, the number of bacteria in the bacterial dilution B' was counted.

Figure 6:
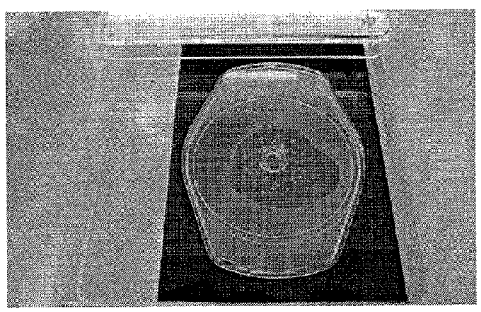
FIG. 6 Pictures for illustrating the results of examinations as to the microbicidal activity achieved by the moth-eye structure. (a) shows the state of sample film No. 1 with a cover. (b) shows the state of comparative example 1 with a cover. (c) shows the state of comparative example 2 with a cover. (d) shows the state of sample film No. 1 without a cover. (e) shows the state of comparative example without a cover. (f) shows the state of comparative example 2 without a cover.
Figure 6:
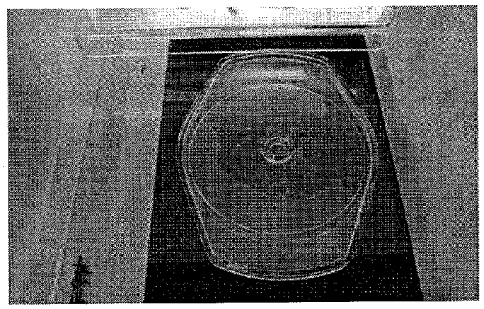
Figure 6:
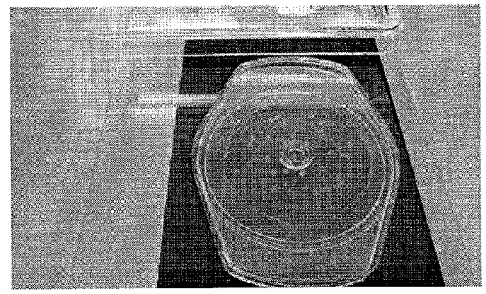
Figure 6:
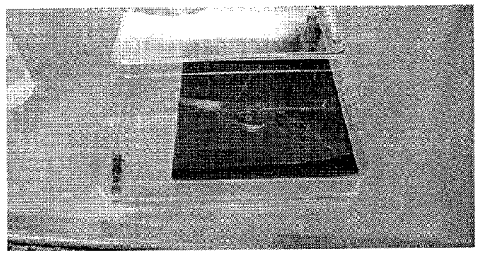
Figure 6:
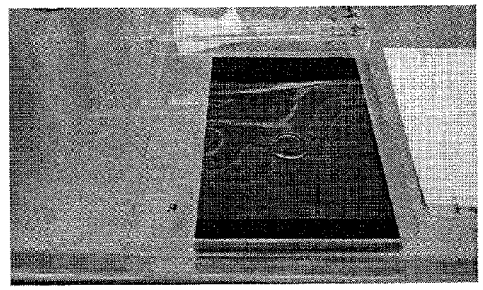
Figure 6:
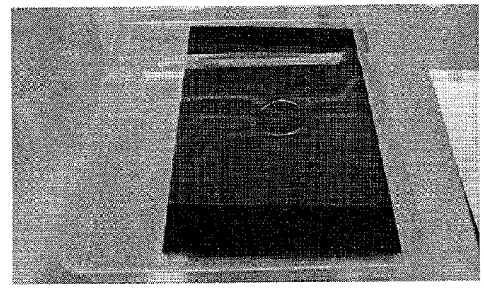

The results are shown in Table 2 below. FIG. 6(a) shows the state of sample film No. 1 with a cover. FIG. 6(b) shows the state of a sample of comparative example 1 with a cover. FIG. 6(c) shows the state of a sample of comparative example 2 with a cover. FIG. 6(d) shows the state of sample film No. 1 without a cover. FIG. 6(e) shows the state of a sample of comparative example 1 without a cover. FIG. 6(f) shows the state of a sample of comparative example 2 without a cover.

TABLE 2

|  | SAMPLE FILM NO. 1 | COMPARATIVE EXAMPLE 1 | COMPARATIVE EXAMPLE 2 |
|---|---|---|---|
| WITH COVER | 0 | 7.10E+05 | 1.14E+06 |
| WITHOUT COVER | 2.73E+05 | 2.50E+05 | 8.10E+05 |

As clearly seen from the results of Table 2, only sample film No. 1 produced the microbicidal activity. The microbicidal activity was produced by the moth-eye structure irrespective of the type of the resin material that forms the synthetic polymer film.

Note that sample film No. 1 did not produce the microbicidal activity when the cover was not placed over the bacterial dilution. This is probably because a large number of bacteria were not killed at the surface which had the moth-eye structure, and these bacteria grew.

Next, seven types of sample films No. 5 to No. 11 shown in Table 3 below were evaluated as to the microbicidal ability.

Sample films No. 5 to No. 9 were produced using the same mold as that described above. Synthetic polymer films having different surface free energies were produced by means of using different resin materials for formation of the synthetic polymer films and/or providing a mold release treatment to the surface of the synthetic polymer films.

Sample film No. 5 is a film produced using the fluorine-containing acrylic resin A (which is the same as that used for sample film No. 1) and exhibited generally equal values of the contact angle with respect to water and hexadecane to those of sample film No. 1.

Sample film No. 6 was produced using a resin which was prepared by adding a fluoric lubricant F2 to the acrylic resin B that contains urethane acrylate (which is the same as that used for sample film No. 3 described above). The fluorine-containing nonionic lubricant F2 used was FUTARGENT 250 (manufactured by NEOS Company Limited) commercially available as a fluoric slipping agent (or fluoric surfactant). FUTARGENT has a perfluoroalkenyl structure. The added amount of the fluoric lubricant F2 was 2 mass % with respect to the total resin amount. Further, a surface of the resultant synthetic polymer film was provided with a mold release treatment with the use of the mold releasing agent R1.

Sample film No. 7 was produced using a resin which was prepared by adding the fluoric lubricant F2 (2 mass % with respect to the total resin amount) to the acrylic resin B that contains the same urethane acrylate as that of sample film No. 6. Sample film No. 7 is different from sample film No. 6 in that the mold release treatment was not provided.

Sample film No. 8 was produced using a urethane acrylate-containing acrylic resin C (which is different from the above-described urethane acrylate-containing acrylic resin B).

For sample film No. 9, the fluorine-containing acrylic resin D used was a fluoric coating agent UT-UCH23 manufactured by AGC SEIMI CHEMICAL CO., LTD.

As sample film No. 10, the microbicidal ability of a commercially-available antimicrobial silver ion sheet (material: polypropylene, additive: silver based inorganic antimicrobial agent, product size: about 80×160 mm, 24 sheets contained, purchase price: 108 yen) was evaluated.

Sample film No. 11 was a PET film which was used as the base film of sample films No. 5 to No. 9.

The contact angle of the surfaces of the respective films with respect to water and hexadecane was measured in the same way as that described above.

The procedure of the evaluation of the microbicidal ability was basically the same as that described for Table 2 shown above, except that a bacterial dilution A' in which the concentration of $P.$ $aeruginosa$ bacteria was 1.4E+05 CFU/mL was used instead of the bacterial dilution A. The bacterial dilution A' was dropped onto the respective sample films, and thereafter, a cover was placed thereon. The samples were left in an environment of 37° C. and the relative humidity 100% for 0 hour (5 minutes), 3 hours, 20 hours, or 70 hours and 15 minutes. Thereafter, the bacteria were sufficiently washed away from the sample films. The solution was diluted at a required degree of dilution according to the above-described procedure. The resultant bacterial dilution was dropped onto Petrifilm™ media (product name: Aerobic Count Plate (AC), manufactured by 3M). The bacteria were cultured at 37° C. with the relative humidity of 100%. After 48 hours, the number of bacteria in the bacterial dilution B' was counted. The results are shown in FIG. 8.

Figure 8:
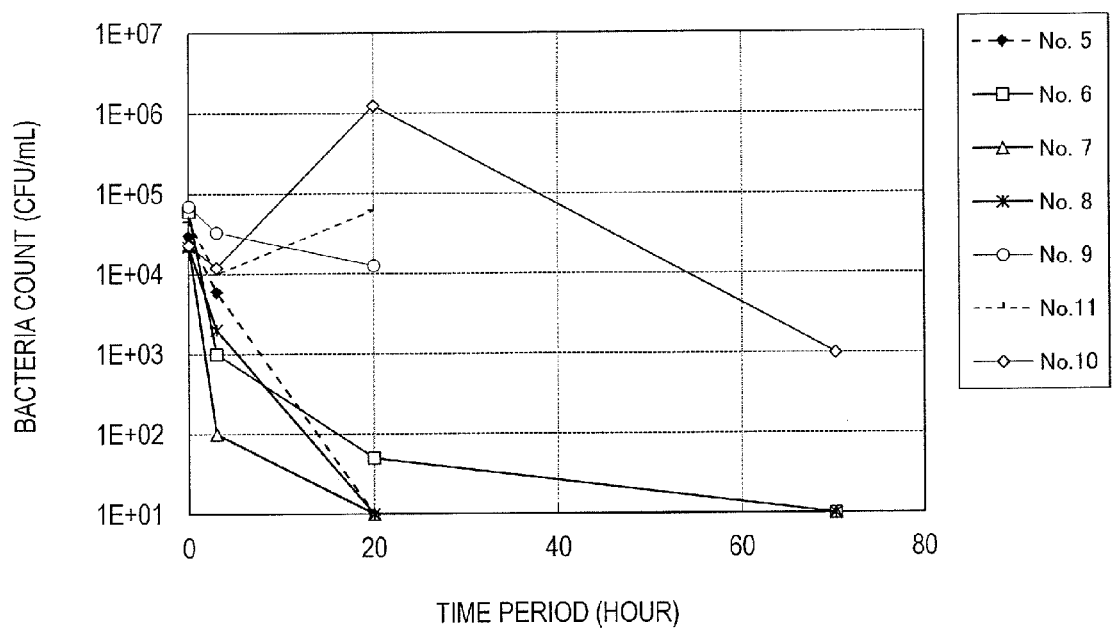
FIG. 8 A graph showing the results of evaluation of the microbicidal ability of the sample films. The horizontal axis represents the time period that the sample film was left (hour). The vertical axis represents the bacteria count (CFU/mL).

FIG. 8 is a graph showing the results of the evaluation of the microbicidal ability of the sample films. The horizontal axis represents the time period that the sample film was left (hour). The vertical axis represents the bacteria count (CFU/mL) in the bacterial dilution B'.

As clearly seen from FIG. 8, sample films No. 5, No. 6, No. 7 and No. 8 have more excellent bactericidal activities than sample No. 10 (commercially-available antimicrobial silver ion sheet). Sample film No. 9 and sample film No. 11 (PET) do not have the microbicidal ability. Although they were left for 70 hours and 15 minutes, the bacteria count increased to such a level that it was uncountable.

As seen from Table 3 below, it was verified that the microbicidal ability has a high correlation with the contact angle of the surface of the synthetic polymer film with respect to hexadecane and that, as previously described, the contact angle of hexadecane with respect to the surface of the synthetic polymer film is preferably not more than 51°, and more preferably not more than 31°. On the other hand, it was also verified that the hydrophilicity (or, conversely, hydrophobicity) of the surface of the synthetic polymer film which is evaluated by the contact angle of water does not directly relate to the microbicidal activity.

TABLE 3

| No. | SYNTHETIC POLYMER FILM (BASE FILM: PET) | CONTACT ANGLE OF WATER (°) | CONTACT ANGLE OF HEXADECANE (°) | MICROBICIDAL ABILITY |
|---|---|---|---|---|
| 5 | FLUORINE-CONTAINING ACRYLIC RESIN A | 133 | 29 | ○ |
| 6 | URETHANE ACRYLATE-CONTAINING ACRYLIC RESIN B WITH FLUORIC LUBRICANT F2 ADDED + MOLD RELEASING AGENT R1 (0.1 mass %) | 91 | 11 | ○ |

TABLE 3-continued

| No. | SYNTHETIC POLYMER FILM (BASE FILM: PET) | CONTACT ANGLE OF WATER (°) | CONTACT ANGLE OF HEXADECANE (°) | MICROBICIDAL ABILITY |
|---|---|---|---|---|
| 7 | URETHANE ACRYLATE-CONTAINING ACRYLIC RESIN B WITH FLUORIC LUBRICANT F2 ADDED | 13 | 11 | ◯ |
| 8 | URETHANE ACRYLATE-CONTAINING ACRYLIC RESIN C | 13 | 8 | ◯ |
| 9 | FLUORINE-CONTAINING ACRYLIC RESIN D | 150 | 71 | X |
| 10 | SILVER ION SHEET | 46 | 43 | Δ |
| 11 | PET | — | — | X |

Note that, in sample film No. 3 and No. 7 described above, the microbicidal effect of a urethane acrylate-containing acrylic resin to which a fluoric lubricant was added was verified. The microbicidal effect of a synthetic polymer film which contained a silicone lubricant instead of the fluoric lubricant was also verified (sample film No. 17 which will be described later). As clearly seen from the results of sample film No. 17, it was verified that an acrylic resin E to which a silicone lubricant was added used for sample films No. 12, No. 14 to No. 17, and No. 51 to No. 62 that will be described later had a microbicidal effect on P. aeruginosa bacteria.

A synthetic polymer film according to an embodiment of the present invention is suitably applicable to uses of suppressing generation of slime on a surface which is in contact with water, for example. For example, the synthetic polymer film is attached onto the inner walls of a water container for a humidifier or ice machine, whereby generation of slime on the inner walls of the container can be suppressed. The slime is attributed to a biofilm which is formed of extracellular polysaccharide (EPS) secreted from bacteria adhering to the inner walls and the like. Therefore, killing the bacteria adhering to the inner walls and the like enables suppression of generation of the slime.

As described above, bringing a liquid into contact with the surface of a synthetic polymer film according to an embodiment of the present invention enables sterilization of the liquid. Likewise, bringing a gas into contact with the surface of a synthetic polymer film according to an embodiment of the present invention enables sterilization of the gas. In general, microorganisms have such a surface structure that they can easy adhere to the surface of an object in order to increase the probability of contact with organic substances which will be their nutrients. Therefore, when a liquid or gas which contains microorganisms is brought into contact with a microbicidal surface of a synthetic polymer film according to an embodiment of the present invention, the microorganisms are likely to adhere to the surface of the synthetic polymer film, and therefore, on that occasion, the liquid or gas is subjected to the microbicidal activity.

Although the microbicidal activity of a synthetic polymer film according to an embodiment of the present invention against P. aeruginosa that is a Gram-negative bacteria has been described in this section, the synthetic polymer film has a microbicidal activity not only on Gram-negative bacteria but also on Gram-positive bacteria and other microorganisms. One of the characteristics of the Gram-negative bacteria resides in that they have a cell wall including an exine. The Gram-positive bacteria and other microorganisms (including ones that do not have a cell wall) have a cell membrane. The cell membrane is formed by a lipid bilayer as is the exine of the Gram-negative bacteria. Therefore, it is estimated that the interaction between the raised portions of the surface of the synthetic polymer film according to an embodiment of the present invention and the cell membrane is basically the same as the interaction between the raised portions and the exine.

Note that, however, the size of the microorganisms varies depending on their types. The size of P. aeruginosa which has been described herein as an example is about 1 μm. However, the size of the bacteria ranges from several hundreds of nanometers to about five micrometers. The size of fungi is not less than several micrometers. It is estimated that the raised portions of the synthetic polymer film which has been described above (the two-dimensional size is about 200 nm) have a microbicidal activity on a microorganism whose size is not less than about 0.5 μm, but there is a probability that the raised portions are too large to exhibit a sufficient microbicidal activity on a bacterium whose size is several hundreds of nanometers. The size of viruses ranges from several tens of nanometers to several hundreds of nanometers, and many of them have a size of not more than 100 nm. Note that viruses do not have a cell membrane but have a protein shell called capsid which encloses virus nucleic acids. It is estimated that the raised portions likewise act on this shell.

In view of the above, the configuration and production method of a synthetic polymer film having raised portions which can exhibit a microbicidal activity against a microorganism of not more than several hundreds of nanometers are described below.

In the following description, raised portions of the above-described synthetic polymer film which have a two-dimensional size in the range of more than 20 nm and less than 500 nm are sometimes referred to as "first raised portions". Raised portions which are superimposedly formed over the first raised portions are referred to as "second raised portions". The two-dimensional size of the second raised portions is smaller than the two-dimensional size of the first raised portions and does not exceed 100 nm. Note that when the two-dimensional size of the first raised portions is less than 100 nm, particularly less than 50 nm, it is not necessary to provide the second raised portions. Recessed portions of the mold corresponding to the first raised portions are referred to as "first recessed portions", and recessed portions of the mold corresponding to the second raised portions are referred to as "second recessed portions".

When the method of forming the first recessed portions which have predetermined size and shape by alternately performing the anodization step and the etching step as described above is applied without any modification, the second recessed portions cannot be formed successfully.

Figure 7:
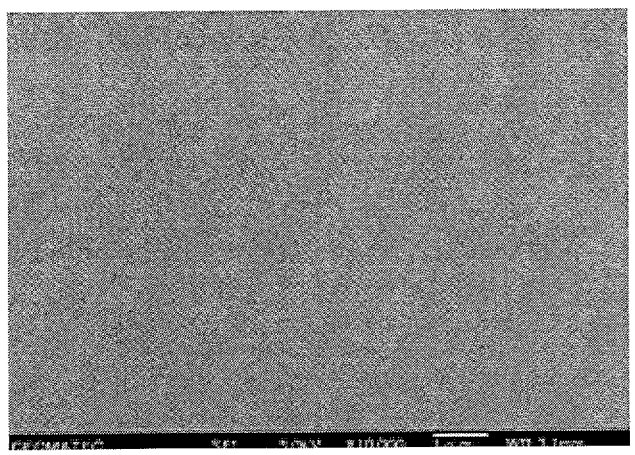
FIG. 7 (a) shows a SEM image of a surface of an aluminum base. (b) shows a SEM image of a surface of an aluminum film. (c) shows a SEM image of a cross section of the aluminum film.
Figure 7:
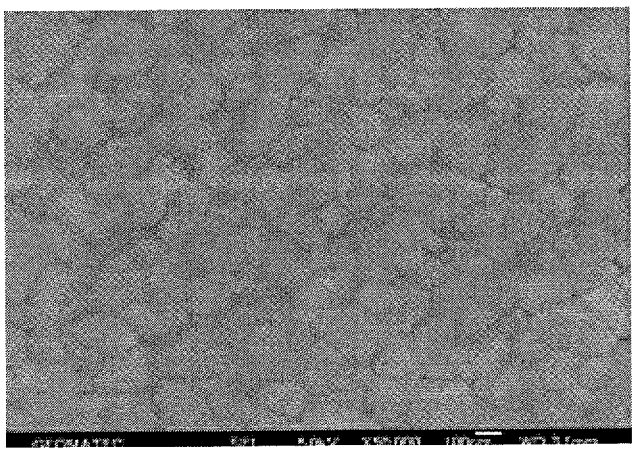
Figure 7:
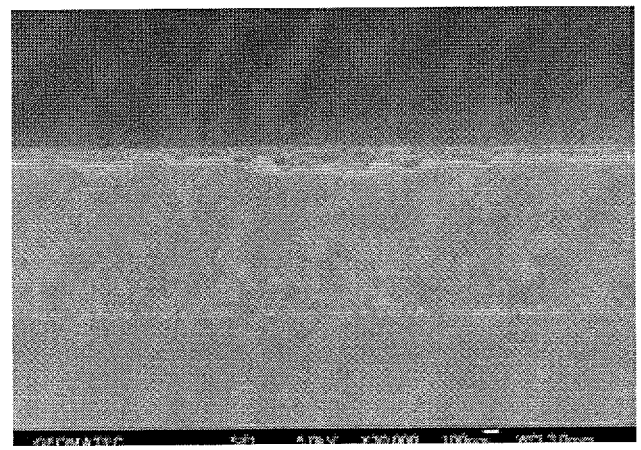

FIG. 7(a) shows a SEM image of a surface of an aluminum base (designated by reference numeral 12 in FIG. 2A). FIG. 7(b) shows a SEM image of a surface of an aluminum film (designated by reference numeral 18 in FIG. 2A). FIG. 7(c) shows a SEM image of a cross section of the aluminum film (designated by reference numeral 18 in FIG. 2A). As seen from these SEM images, there are grains (crystal grains) at the surface of the aluminum base and the surface of the aluminum film. The grains of the aluminum film form unevenness at the surface of the aluminum film. This unevenness at the surface affects formation of the recessed portions in the anodization and therefore interrupts formation of second recessed portions whose $D_p$ or $D_{int}$ is smaller than 100 nm.

In view of the above, a mold manufacturing method according to an embodiment of the present invention includes: (a) providing an aluminum base or an aluminum film deposited on a support; (b) the anodization step of applying a voltage at the first level while a surface of the aluminum base or aluminum film is kept in contact with an electrolytic solution, thereby forming a porous alumina layer which has the first recessed portions; (c) after step (b), the etching step of bringing the porous alumina layer into contact with an etching solution, thereby enlarging the first recessed portions; and (d) after step (c), applying a voltage at the second level that is lower than the first level while the porous alumina layer is kept in contact with an electrolytic solution, thereby forming the second recessed portions in the first recessed portions. For example, the first level is higher than 40 V, and the second level is equal to or lower than 20 V.

Specifically, an anodization step is carried out with the voltage at the first level, whereby the first recessed portions are formed which have such a size that is not influenced by the grains of the aluminum base or aluminum film. Thereafter, the thickness of the barrier layer is decreased by etching, and then, another anodization step is carried out with the voltage at the second level that is lower than the first level, whereby the second recessed portions are formed in the first recessed portions. When the second recessed portions are formed through such a procedure, the influence of the grains is avoided.

Figure 9:
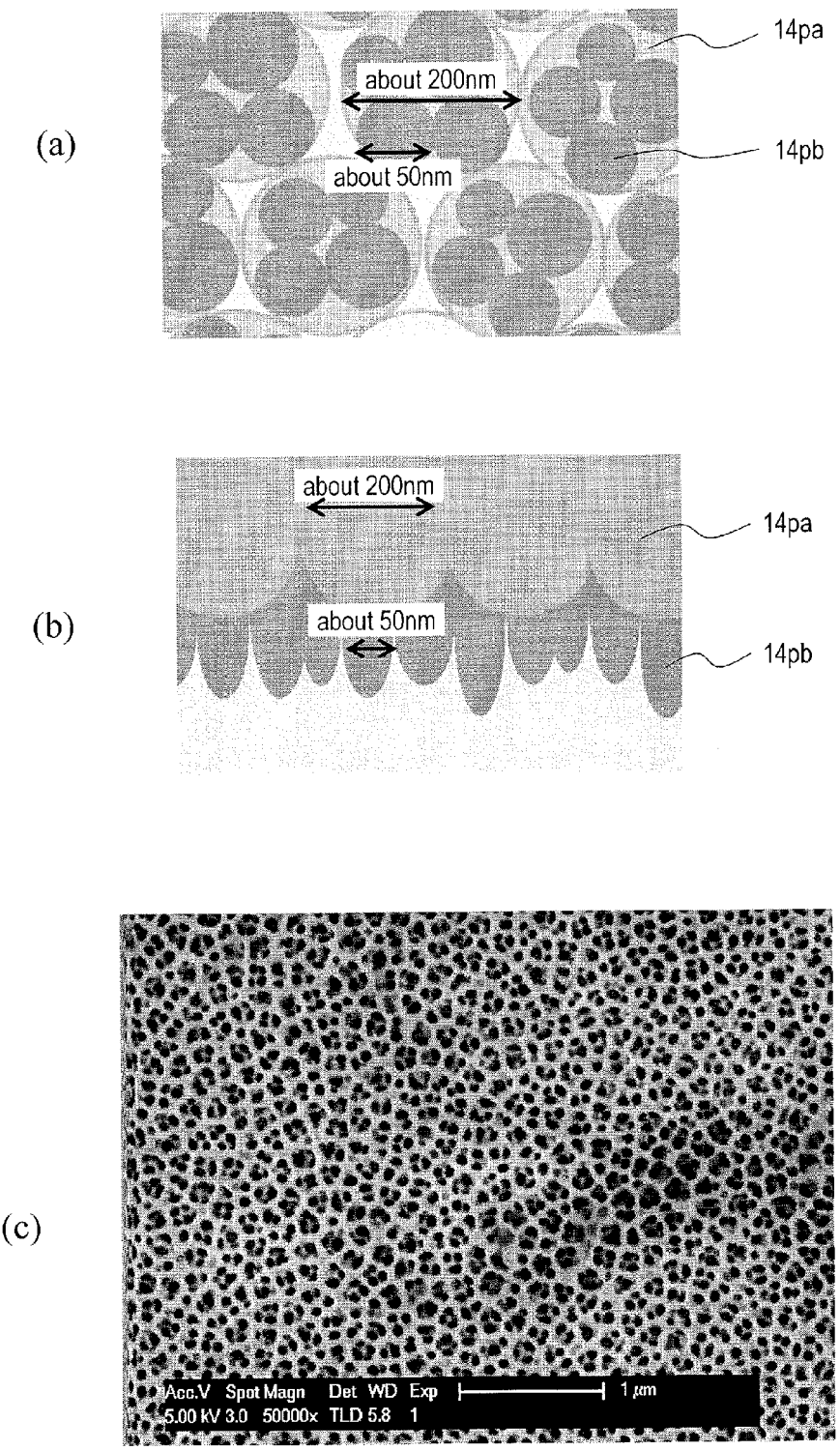
FIG. 9 (a) is a schematic plan view of a porous alumina layer of a mold. (b) is a schematic cross-sectional view of the porous alumina layer. (c) is a SEM image of a prototype mold.

A mold which has first recessed portions 14pa and second recessed portions 14pb formed in the first recessed portions 14pa is described with reference to FIG. 9. FIG. 9(a) is a schematic plan view of a porous alumina layer of a mold. FIG. 9(b) is a schematic cross-sectional view of the porous alumina layer. FIG. 9(c) shows a SEM image of a prototype mold.

As shown in FIGS. 9(a) and 9(b), the surface of the mold of the present embodiment has the plurality of first recessed portions 14pa whose two-dimensional size is in the range of more than 20 nm and less than 500 μm and the plurality of second recessed portions 14pb which are superimposedly formed over the plurality of first recessed portions 14pa. The two-dimensional size of the plurality of second recessed portions 14pb is smaller than the two-dimensional size of the plurality of first recessed portions 14pa and does not exceed 100 nm. The height of the second recessed portions 14pb is, for example, more than 20 nm and not more than 100 nm. The second recessed portions 14pb preferably have a generally conical portion as do the first recessed portions 14pa.

The porous alumina layer shown in FIG. 9(c) was formed as described below.

The aluminum film used was an aluminum film which contains Ti at 1 mass %. The anodization solution used was an oxalic acid aqueous solution (concentration: 0.3 mass %, solution temperature: 10° C.). The etching solution used was a phosphoric acid aqueous solution (concentration: 10 mass %, solution temperature: 30° C.). After the anodization was carried out with a voltage of 80 V for 52 seconds, the etching was carried out for 25 minutes. Then, the anodization was carried out with a voltage of 80 V for 52 seconds, and the etching was carried out for 25 minutes. Thereafter, the anodization was carried out with a voltage of 20 V for 52 seconds, and the etching was carried out for 5 minutes. Further, the anodization was carried out with a voltage of 20 V for 52 seconds.

As seen from FIG. 9(c), the second recessed portions whose $D_p$ was about 50 nm were formed in the first recessed portions whose $D_p$ was about 200 nm. When in the above-described manufacturing method the voltage at the first level was changed from 80 V to 45 V for formation of the porous alumina layer, the second recessed portions whose $D_p$ was about 50 nm were formed in the first recessed portions whose $D_p$ was about 100 nm.

When a synthetic polymer film is produced using such a mold, the produced synthetic polymer film has raised portions whose configuration is the inverse of that of the first recessed portions 14pa and the second recessed portions 14pb shown in FIGS. 9(a) and 9(b). That is, the produced synthetic polymer film further includes a plurality of second raised portions superimposedly formed over a plurality of first raised portions.

The thus-produced synthetic polymer film which has the first raised portions and the second raised portions superimposedly formed over the first raised portions has a microbicidal activity on various microorganisms, ranging from relatively small microorganisms of about 100 nm to relatively large microorganisms of not less than 5 μm.

As a matter of course, only raised portions whose two-dimensional size is in the range of more than 20 nm and less than 100 nm may be formed according to the size of a target microorganism. The mold for formation of such raised portions can be manufactured, for example, as described below.

The anodization is carried out using a neutral salt aqueous solution (ammonium borate, ammonium citrate, etc.), such as an ammonium tartrate aqueous solution, or an organic acid which has a low ionic dissociation degree (maleic acid, malonic acid, phthalic acid, citric acid, tartaric acid, etc.) to form a barrier type anodized film. After the barrier type anodized film is removed by etching, the anodization is carried out with a predetermined voltage (the voltage at the second level described above), whereby recessed portions whose two-dimensional size is in the range of more than 20 nm and less than 100 nm can be formed.

For example, an aluminum film which contains Ti at 1 mass % is anodized at 100 V for 2 minutes using a tartaric acid aqueous solution (concentration: 0.1 mol/l, solution temperature: 23° C.), whereby a barrier type anodized film is formed. Thereafter, the etching is carried out for 25 minutes using a phosphoric acid aqueous solution (concentration: 10 mass %, solution temperature: 30° C.), whereby the barrier type anodized film is removed. Thereafter, the anodization and the etching are alternatively repeated as described above, specifically through 5 anodization cycles and 4 etching cycles. The anodization was carried out at 20 V for 52 seconds using an oxalic acid aqueous solution (concentration: 0.3 mass %, solution temperature: 10° C.) as the anodization solution. The etching was carried out for 5 minutes using the above-described etching solution. As a result, recessed portions whose two-dimensional size is about 50 nm can be formed.

Microbicidal Effect on Black Mold

Hereinafter, it is explained with experimental examples that a synthetic polymer film according to an embodiment of the present invention also has the microbicidal ability against black mold (*Cladosporium*). Sample films No. 12 and No. 13 shown in Table 4 below were evaluated as to the microbicidal ability against black mold.

Sample film No. 12 was a film produced using the acrylic resin E to which a silicone lubricant was added. Sample film No. 12 was produced using the same mold as that described above. The contact angle of the surface of sample film No. 12 with respect to water and hexadecane was measured through the same procedure as that described above.

Sample film No. 13 was a PET film which was used as the base film of sample film No. 12.

The microbicidal ability of sample films No. 12 and No. 13 against black mold was evaluated through the following procedure:

1. Undiluted bacterial solution was prepared. Black mold cultured on an agar medium (potato dextrose agar: PDA) was collected using a cotton swab soaked with sterilized water and put into a conical tube. Sterilized water was put into the conical tube, when necessary, for the sake of convenience in use, whereby an undiluted bacterial solution was obtained (the bacteria count of the black mold was on the order of 1E+07 CFU/mL to 1E+08 CFU/mL);

2. The undiluted bacterial solution was diluted stepwise with sterilized water, whereby bacterial dilution A3 was prepared (the bacteria count of the black mold was on the order of 1E+05 CFU/mL). The bacteria count in the bacterial dilution A3, which was examined through the procedure of step 8 below, was 2.8E+05 cfu/mL;

3. A 400 μL drop of the bacterial dilution A3 was placed on each of the sample films, and a cover (e.g., cover glass) was placed over the bacterial dilution A3 to adjust the amount of the bacterial dilution A3 per unit area (about 0.4 mL/cm$^2$).

4. The samples were left in an environment where the temperature was 37° C. and the relative humidity was 100% for a predetermined time period (the time period: 67 hours).

5. The entire sample film with the bacterial dilution A3 and 9.6 mL sterilized water were put into a filter bag. The sample films were rubbed with hands over the filter bag to sufficiently wash away the bacteria from the sample films. The total solution remaining in the filter bag was 10 mL, i.e., a 25-fold dilution of the bacterial dilution A3. This postwash solution in the filter bag is referred to as "bacterial dilution B3".

6. 1 mL of the bacterial dilution B3 was put into 9 mL sterilized water, whereby bacterial dilution C3 was prepared.

7. 1 mL of the bacterial dilution C3 was put into 9 mL sterilized water, whereby bacterial dilution D3 was prepared. Further, 1 mL of the bacterial dilution D3 was put into 9 mL sterilized water, whereby bacterial dilution E3 was prepared.

8. 1 mL drops of the bacterial dilution B3 and the bacterial dilution E3 were placed on Petrifilm™ media (product name: Rapid Yeast and Mold Count Plate (RYM), manufactured by 3M). The bacteria were cultured at 25° C. with the relative humidity of 100% for 48 hours, and the number of bacteria was counted.

Figure 10:
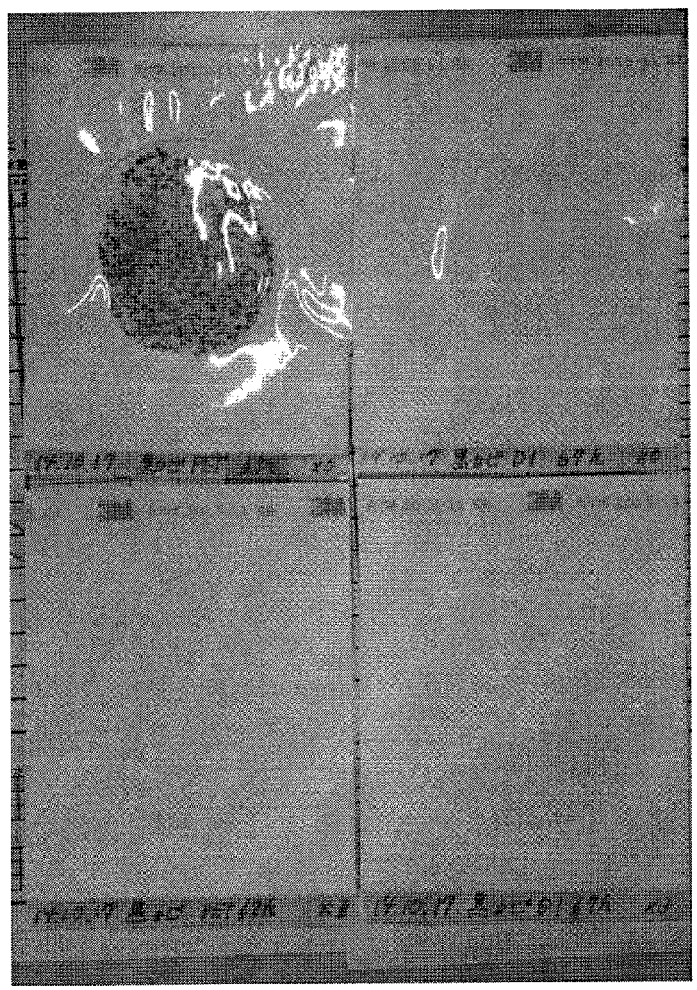
FIG. 10 Pictures for illustrating the evaluation results of the microbicidal ability of sample films No. 12 and No. 13. Specifically, optical images of the surfaces of Petrifilm™ media on which black mold was cultured.

The results of the 48-hour culture at step 8 described above are shown in FIG. 10. The right-hand part of FIG. 10 shows the evaluation results of sample film No. 12 (upper: bacterial dilution B3, lower: bacterial dilution E3). The left-hand part of FIG. 10 shows the evaluation results of sample film No. 13 (upper: bacterial dilution B3, lower: bacterial dilution E3).

Refer to FIG. 10. As for sample film No. 12, the bacteria count in the bacterial dilution B3 and the bacteria count in the bacterial dilution E3 were both 0 CFU/mL. It is understood that sample film No. 12 has a microbicidal effect on black mold. On the other hand, as for sample film No. 13, the bacteria count in the bacterial dilution E3 was 1 CFU/mL. Since the bacterial dilution E3 is obtained by diluting the bacterial dilution B3 1000-fold, it is estimated that the bacteria count in the bacterial dilution B3 was on the order of 1E+03 CFU/mL or more. Sample film No. 13 does not have microbicidal ability against black mold.

TABLE 4

| No. | SYNTHETIC POLYMER FILM (BASE FILM: PET) | CONTACT ANGLE OF WATER (°) | CONTACT ANGLE OF HEXADECANE (°) | MICROBICIDAL ABILITY |
|---|---|---|---|---|
| 12 | ACRYLIC RESIN E WITH SILICONE LUBRICANT ADDED | 45.36 | 10.32 | ○ |
| 13 | PET | — | — | X |

Method for Reactivating Surface which has Microbicidal Effect

As previously described with reference to FIG. 5, microorganisms die at the surface of a synthetic polymer film according to an embodiment of the present invention. This is because the surface of the synthetic polymer film has the microbicidal ability against the microorganisms. It is seen from FIG. 5 that a dead microorganism covers the tip ends of the raised portions provided over the surface of the synthetic polymer film. It is estimated from this fact that the dead microorganism adheres to the surface of the synthetic polymer film, and there is a probability that the microbicidal effect on microorganisms decreases. It is also estimated that, as the method of sterilizing a gas or liquid by bringing the gas or liquid into contact with the surface of the synthetic polymer film is used more, the number of microorganisms adhering to the surface of the synthetic polymer film increases, and there is a probability that the microbicidal effect of the synthetic polymer film decreases.

Figure 5:
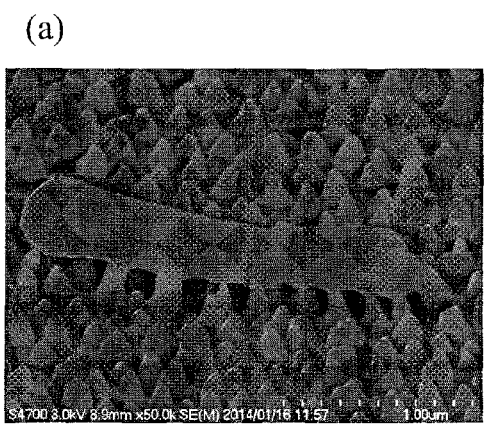
FIG. 5 (a) to (d) show SEM images obtained by SEM (Scanning Electron Microscope) observation of a P. aeruginosa bacterium which died at a surface which had a moth-eye structure.
Figure 5:
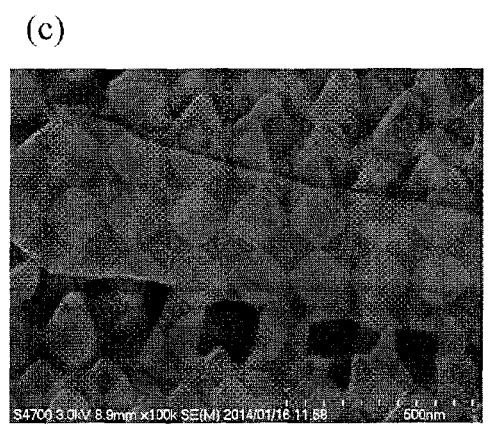
Figure 5:
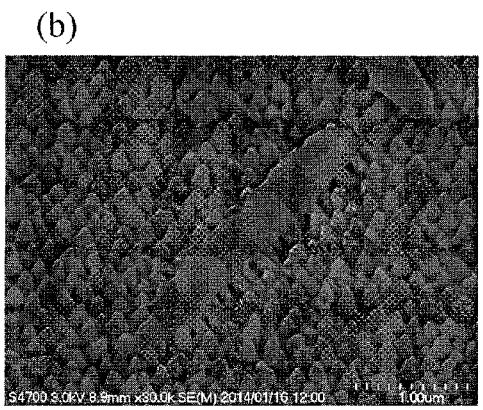
Figure 5:
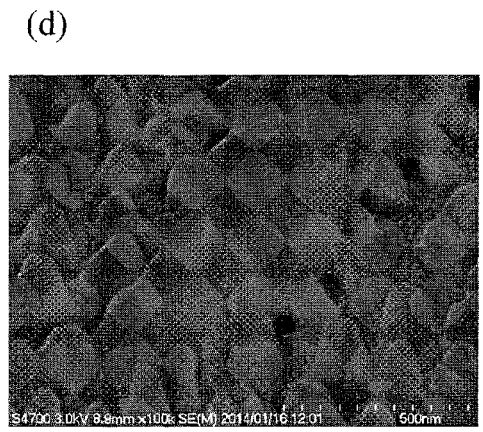

It is also seen from FIG. 5 that the tip ends of the raised portions provided over the surface of the synthetic polymer film are present inside the cell wall (exine) of a *P. aeruginosa* bacterium. That is, the *P. aeruginosa* bacterium is not only in contact with the tip ends of the raised portions but also partially present between the raised portions. It is estimated from this that there is a probability that removing microorganisms from the surface of the synthetic polymer film is not easy.

The present inventors studied the method for reactivating a surface of a synthetic polymer film which has a microbicidal effect and/or the method for recycling a synthetic polymer film whose surface has a microbicidal effect. Specifically, the present inventors studied, for example, the method for efficiently removing microorganisms from the surface of the synthetic polymer film.

A method for reactivating a surface of a synthetic polymer film which has a microbicidal effect according to an embodiment of the present invention includes the steps of: (A) providing a synthetic polymer film, the synthetic polymer film having a surface over which a plurality of raised portions are provided, a two-dimensional size of the plurality of raised portions being in a range of more than 20 nm and less than 500 nm when viewed in a normal direction of the synthetic polymer film, the surface having a microbicidal effect, the surface having a microorganism adhering thereto; and (B) removing the microorganism by wiping the surface. Step (B) includes removing the microorganism by wiping the surface with, for example, a cloth soaked with water or alcohol (e.g., isopropyl alcohol). Step (B) preferably includes removing the microorganism by wiping the surface with a cloth soaked with water.

Hereinafter, experimental examples are presented, and the result of the study of the method for reactivating (washing) a surface of a synthetic polymer film which has a microbicidal effect is described. The effects of different reactivation methods (washing methods) were evaluated using sample films No. 51 to No. 62.

Sample films No. 51 to No. 62 were produced using the acrylic resin E to which a silicone lubricant was added (the same acrylic resin as that used for sample film No. 12) with the use of the same mold as that described above.

1. The sample films were immersed in a bacterial dilution (containing P. aeruginosa bacteria on the order of 1E+05 CFU/mL) for 7 days.

2. Three square films of 0.5 cm on each side were randomly cut out from each of the sample films. The three films were affixed to an electrically-conductive tape.

3. The three films on the electrically-conductive tape were washed using respective surface reactivation methods (washing methods).

4. Five portions were randomly selected from each of the three films (15 portions in total from each of the sample films), and SEM images of the selected portions were obtained.

The surface reactivation methods for respective sample films and the evaluation results are shown in Table 5 below.

TABLE 5

| No. | SURFACE REACTIVATION METHOD | RESULT |
|---|---|---|
| 51 | NONE | — |
| 52 | IMMERSED IN PURE WATER FOR 180 MIN., AND THEREAFTER DRIED BY AIR BLOWER | X |
| 53 | IMMERSED IN CONTACT LENS WASHING SOLUTION FOR 180 MIN. AND THEREAFTER DRIED BY AIR BLOWER | X |
| 54 | IMMERSED IN CONTACT LENS WASHING SOLUTION FOR 60 MIN. AND THEREAFTER DRIED BY AIR BLOWER | X |
| 55 | IMMERSED IN CONTACT LENS WASHING SOLUTION FOR 60 MIN. AND THEREAFTER IMMERSED IN PURE WATER FOR 60 MIN. | X |
| 56 | IMMERSED IN CONTACT LENS WASHING SOLUTION FOR 60 MIN. AND THEREAFTER WIPED WITH CLOTH SOAKED WITH IPA | Δ |
| 57 | IMMERSED IN CONTACT LENS WASHING SOLUTION FOR 60 MIN. AND THEREAFTER WIPED WITH CLOTH SOAKED WITH PURE WATER | Δ |
| 58 | WIPED WITH CLOTH SOAKED WITH IPA | Δ |

TABLE 5-continued

| No. | SURFACE REACTIVATION METHOD | RESULT |
|---|---|---|
| 59 | WIPED WITH CLOTH SOAKED WITH PURE WATER | ⊚ |
| 60 | WASHED WITH FLOWING PURE WATER FOR 5 MIN. | X |
| 61 | ULTRASONIC WASHING WITH PURE WATER FOR 5 MIN. | X |
| 62 | WIPED WITH CLOTH SOAKED WITH PURE WATER | ⊚ |

Figure 11:
FIG. 11 One of the SEM images obtained from sample film No. 51.
Figure 12:
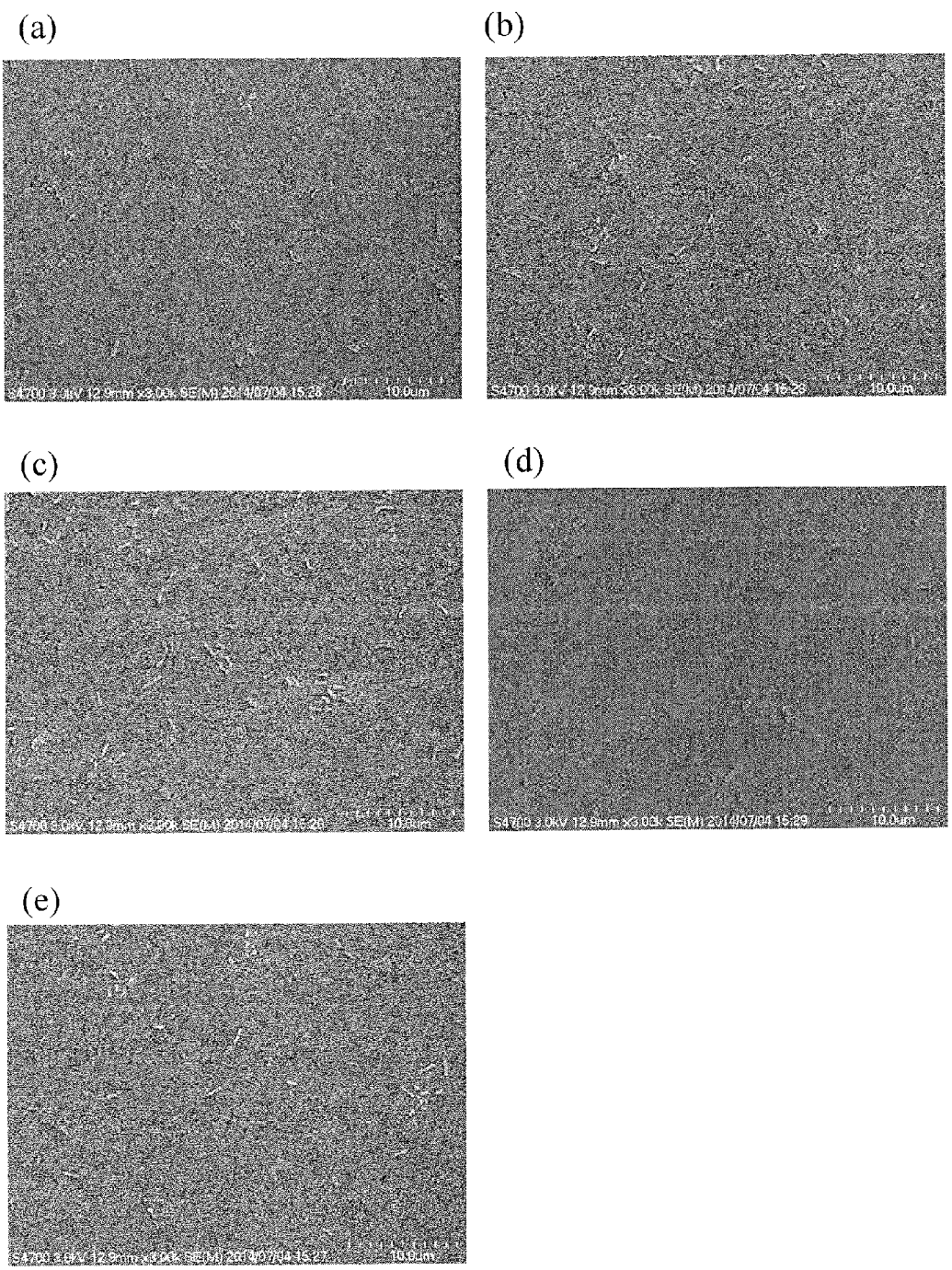
FIG. 12 (a) to (e) are five of the SEM images obtained from sample film No. 52.

Sample film No. 51 was not washed for the sake of comparison. In the case where a surface reactivation method (washing method) was not used, it was confirmed from an obtained SEM image that there were P. aeruginosa bacteria adhering to the surface of the film. FIG. 11 shows one of the SEM images obtained from sample film No. 51. As confirmed from FIG. 11, P. aeruginosa bacteria have, for example, an elongated shape and adhere to the surface of the film. Each of P. aeruginosa bacteria had, for example, a shape of about several micrometers×several hundreds of nanometers (e.g., 1 μm×0.2 μm). A region of 150 μm×110 μm (sometimes referred to as "observation region") was selected from each of 15 SEM image portions, and the number of bacteria adhering in this region was counted. The bacteria counts were 30, 41, 25, 55, 16, 11, 23, 22, 30, 26, 20, 14, 30, 10, and 12. The average bacteria count of the 15 portions was 24. The minimum bacteria count was 10.

As for sample films No. 52 to No. 62 described below, the surface reactivation methods (washing methods) were evaluated by comparison with sample film No. 51. In Table 5, "⊚", "Δ", and "X" represent the following assessments:

⊚: In each of the 15 observation regions, the bacteria count was not more than 5, and any other organic matter than the bacteria adhering to the raised portions was not detected.

Δ: In some observation regions, the bacteria count was not more than 5 and any other organic matter than the bacteria adhering to the raised portions was not detected, while there was an observation region in which the bacteria count was not less than 6 or an observation region in which there was organic matter (including a washing solution and bacteria) adhering to the raised portions.

X: In each of the 15 observation regions, the bacteria count was not less than 10 (the minimum value in sample film No. 51). Or, in each of the 15 observation regions, it was observed that there was organic matter (including a washing solution and bacteria) adhering to the raised portions over a relatively wide area (for example, adhering so as to fill the gap between the raised portions or clinging to the tip ends of the raised portions and spreading over the raised portions).

Sample film No. 52 was immersed in pure water for 180 minutes and thereafter dried by an air blower. FIGS. 12(a) to 12(e) show five of the SEM images obtained from sample film No. 52. It can be confirmed that there are P. aeruginosa bacteria adhering to the film. In each of the 15 SEM image portions, the number of bacteria adhering in a region of 150 μm×110 μm was counted in the same way as in sample film No. 51. The bacteria counts were not less than 49, 24, 81, 28, not less than 25, 30, 67, 21, not less than 37, not less than 20, 39, 40, 36, 71, and 28. The average bacteria count of the 15 portions was not less than 40. Here, the words "not less than" for the bacteria count refer to a case where an adhering object which is larger than the shape of each of P. aeruginosa bacteria was detected in the region. This large adhering object is considered to include a clump of a plurality of P. aeruginosa bacteria. In sample film No. 52, the bacteria count was not less than 10 in each of the 15 observation regions. One of the possible reasons why the bacteria count was larger in sample film No. 52 than in sample film No. 51 is that *P. aeruginosa* bacteria did not uniformly adhere across the film surface. That is, it is probable that the number of adhering bacteria and the shape of adhering bacteria depend on the selected portion.

Sample film No. 53 was immersed in a contact lens washing solution (ROHTO C-cube™ Soft One Moist manufactured by ROHTO Pharmaceutical Co., Ltd.) for 180 minutes and thereafter dried by an air blower. Organic matter was found adhering to the surface of sample film No. 53 over a relatively large area as compared with sample film No. 51. The organic matter is considered to include not only the contact lens washing solution but also *P. aeruginosa* bacteria themselves and components contained in the *P. aeruginosa* bacteria.

Sample film No. 54 was immersed in a contact lens washing solution (which was the same as that used for sample film No. 53) for 60 minutes and thereafter dried by an air blower. There were *P. aeruginosa* bacteria adhering to the surface of sample film No. 54. The *P. aeruginosa* bacteria appeared to be clinging to the tip ends of the raised portions provided over the surface of the film and spreading over the raised portions. Any other object than the *P. aeruginosa* bacteria was also found adhering to the basal side of the raised portions (for example, when the raised portions have a conical shape, near the base of the cone) so as to fill the gap between the raised portions.

Figure 13:
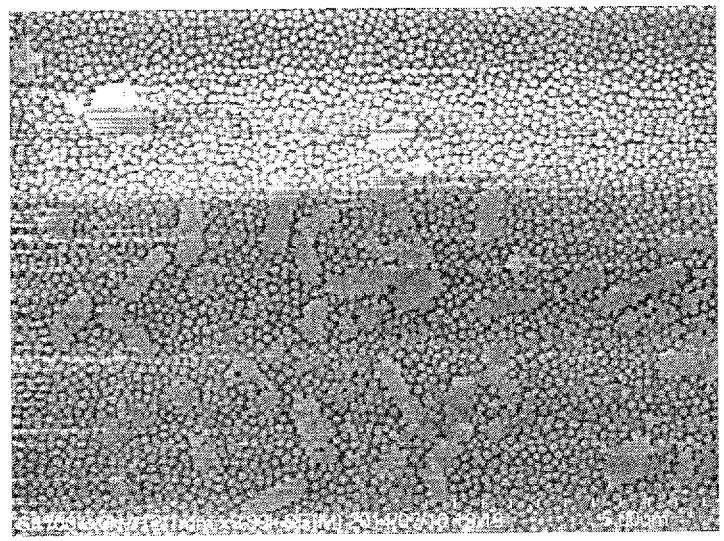
FIG. 13 (a) is one of the SEM images obtained from sample film No. 55. (b) is an enlarged view of (a).
Figure 13:
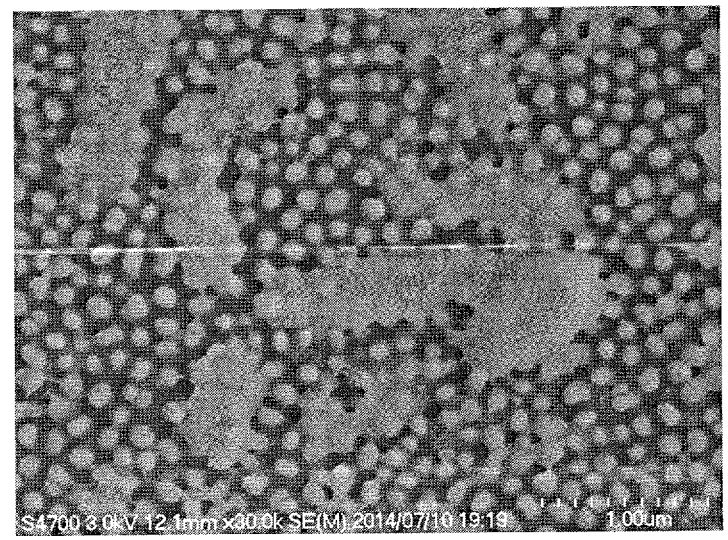

Sample film No. 55 was immersed in a contact lens washing solution (which was the same as that used for sample film No. 53) for 60 minutes and thereafter immersed in pure water for 60 minutes. FIGS. 13(a) and 13(b) show one of the SEM images obtained from sample film No. 55. FIG. 13(b) is an enlarged view of FIG. 13(a). It can be seen that there are *P. aeruginosa* bacteria adhering to the surface of sample film No. 55. There are *P. aeruginosa* bacteria which appear to be clinging to the tip ends of the raised portions provided over the surface of the film. Part of the *P. aeruginosa* bacteria appears to reside in the gap between the raised portions. Sample film No. 55 is different from sample film No. 54 in that there was no adhering object that fills the gap between the raised portions at the basal side of the raised portions. As estimated from the comparison between the results of sample films No. 54 and No. 55, an adhering object that fills the gap between the raised portions, such as found in sample film No. 54, may be part of the contact lens washing solution remaining at the surface.

Sample film No. 56 was immersed in a contact lens washing solution (which was the same as that used for sample film No. 53) for 60 minutes and thereafter wiped with a wiping cloth (Savina MX manufactured by KB SEIREN, LTD., Savina is a registered trademark) soaked with IPA (isopropyl alcohol). In some parts of the surface of sample film No. 56, there were remaining *P. aeruginosa* bacteria. However, it can be said that *P. aeruginosa* bacteria were effectively removed from sample film No. 56 as compared with sample films No. 51 to No. 55 that were not wiped with a cloth.

Figure 14:
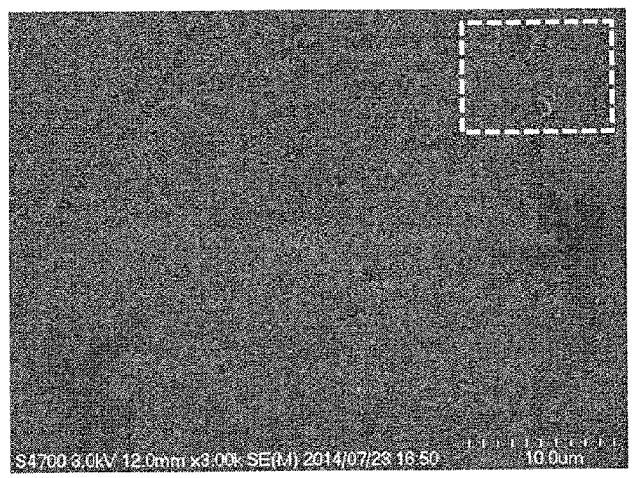
FIG. 14 (a) is one of the SEM images obtained from sample film No. 57. (b) is an enlarged view of a region enclosed by a broken line in (a). (c) is an enlarged view of a region enclosed by a broken line in (b).
Figure 14:
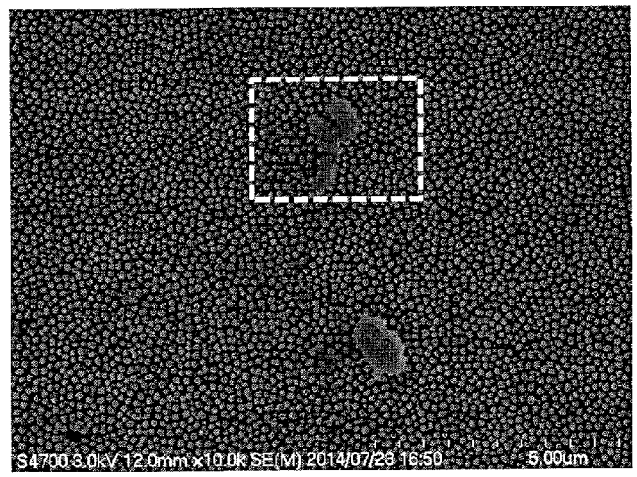
Figure 14:
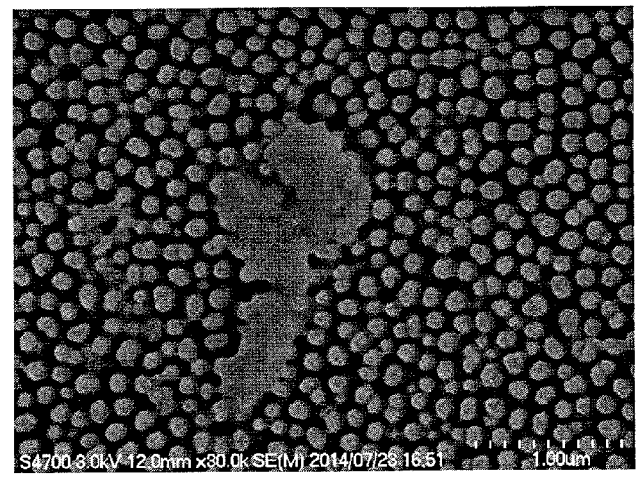
Figure 15:
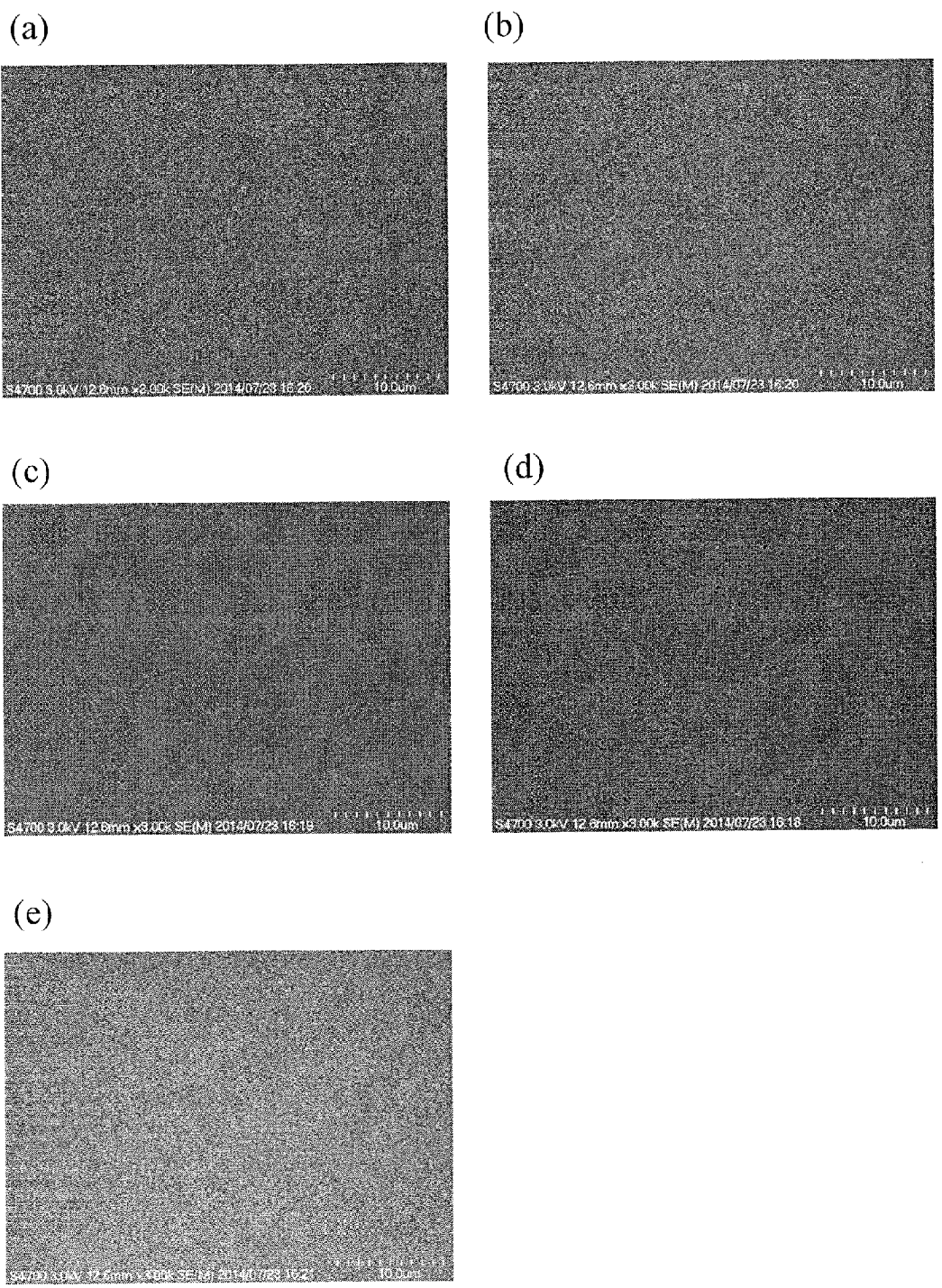
FIG. 15 (a) to (e) are five of the SEM images obtained from sample film No. 59.

Sample film No. 57 was immersed in a contact lens washing solution (which was the same as that used for sample film No. 53) for 60 minutes and thereafter wiped with a wiping cloth (which was the same as that used for sample film No. 56) soaked with pure water. FIGS. 14(a) to 14(c) show one of the SEM images obtained from sample film No. 57. FIG. 14(b) is an enlarged view of a region enclosed by a broken line in FIG. 14(a). FIG. 14(c) is an enlarged view of a region enclosed by a broken line in FIG. 14(b). As seen from FIG. 14, in some parts of the surface of sample film No. 57, there were remaining *P. aeruginosa* bacteria. However, it can be said that *P. aeruginosa* bacteria were effectively removed from sample film No. 57 as compared with sample films No. 51 to No. 55 that were not wiped with a cloth. Note that, however, there were more *P. aeruginosa* bacteria remaining without being removed as compared with sample film No. 56. As seen from FIGS. 14(b) and 14(c), unremoved *P. aeruginosa* bacteria remaining on the surface appear to be clinging to the tip ends of the raised portions.

Sample film No. 58 was wiped with a wiping cloth (which was the same as that used for sample film No. 56) soaked with IPA (isopropyl alcohol). In some parts of the surface of sample film No. 58, there were remaining *P. aeruginosa* bacteria. However, it can be said that *P. aeruginosa* bacteria were effectively removed from sample film No. 58 as compared with sample films No. 51 to No. 55 that were not wiped with a cloth.

Sample film No. 59 was wiped with a wiping cloth (which was the same as that used for sample film No. 56) soaked with pure water. FIGS. 15(a) to 15(e) show five of the SEM images obtained from sample film No. 59. As seen from FIG. 15, *P. aeruginosa* bacteria were effectively removed from the surface of sample film No. 59. The *P. aeruginosa* bacteria were substantially thoroughly removed from the surface of sample film No. 59. In each of the 15 observation regions, the bacteria count of *P. aeruginosa* bacteria remaining on the surface of the film was not more than 5.

Sample film No. 60 was washed with flowing pure water for 5 minutes. There were *P. aeruginosa* bacteria adhering to the surface of sample film No. 60. The *P. aeruginosa* bacteria appeared to be clinging to the tip ends of the raised portions provided over the surface of the film.

Sample film No. 61 was subjected to ultrasonic washing with pure water for 5 minutes. There were *P. aeruginosa* bacteria adhering to the surface of sample film No. 61. The *P. aeruginosa* bacteria appeared to be clinging to the tip ends of the raised portions provided over the surface of the film.

Sample film No. 62 was wiped with a wiping cloth soaked with pure water as was sample film No. 59. The *P. aeruginosa* bacteria were substantially thoroughly removed from the surface of sample film No. 62. In each of the 15 observation regions, the bacteria count of *P. aeruginosa* bacteria remaining on the surface of the film was not more than 5. The reproducibility of the surface reactivation method (washing method) which is realized by wiping with a wiping cloth soaked with pure water was verified.

As seen from the above-described experimental examples, wiping the surface of the synthetic polymer film is an effective way of removing microorganisms from the surface. Wiping the surface of the synthetic polymer film with water (water wiping) is a more effective way of removing microorganisms from the surface. For example, the surface of the synthetic polymer film may be wiped with a cloth soaked with water. Physically removing microorganisms from the surface was more effective than removing microorganisms from the surface by a chemical treatment. To figure out the reasons for this, the present inventors examined the state of microorganisms adhering to a surface of the synthetic polymer film which has a microbicidal effect in more detail.

FIGS. 16(a) to 16(d) show SEM images of a *P. aeruginosa* bacterium which died at a surface of sample film No. 51 which had a moth-eye structure. FIG. 16(a) and FIG. 16(b) are enlarged views of FIG. 16(c). FIG. 16(d) is an enlarged view of FIG. 16(a) and FIG. 16(b).

As clearly seen from FIGS. 16(a) to 16(d), the raised portions of the synthetic polymer film tilt (warp) as if they were drawn to the *P. aeruginosa* bacterium. Raised portions of a synthetic polymer film according to an embodiment of the present invention whose two-dimensional size is in the range of more than 20 nm and less than 500 nm (first raised portions) are capable of warping (tilting) when they come in contact with microorganisms. As clearly seen from FIGS. 16(*b*) and 16(*c*), raised portions with no *P. aeruginosa* bacterium adhering thereto extend generally parallel to a normal direction of the synthetic polymer film, while some of raised portions with a *P. aeruginosa* bacterium adhering thereto tilt (warp) toward the *P. aeruginosa* bacterium. Tilting (warping) of raised portions enable more raised portions to come in contact with microorganisms. It is estimated that a synthetic polymer film which has over its surface raised portions which are capable of tilting (warping) toward microorganisms has a more excellent microbicidal effect.

Figure 16:
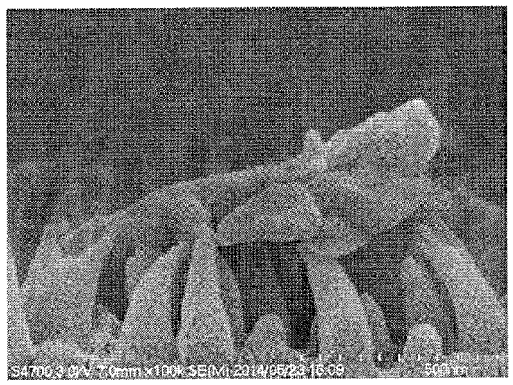
FIG. 16 (a) to (d) show SEM images of a P. aeruginosa bacterium which died at a surface of sample film No. 51 which had a moth-eye structure.
Figure 16:
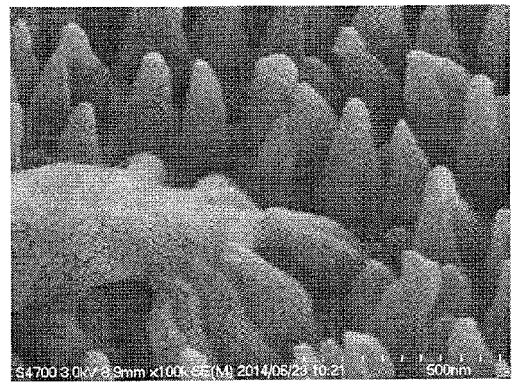
Figure 16:
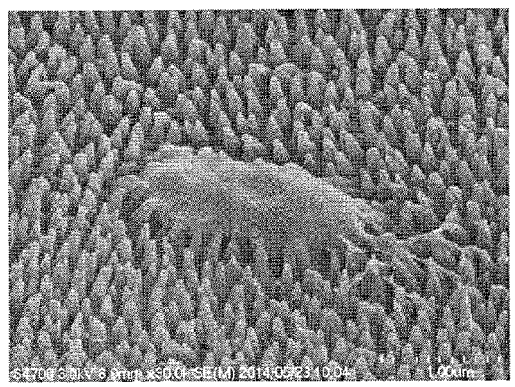
Figure 16:
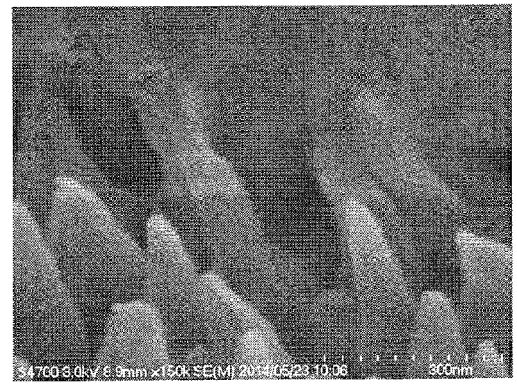

The tilt (warp) of the raised portions which was observed in FIGS. 16(*a*) to 16(*d*) was not found after *P. aeruginosa* bacteria were removed by, for example, wiping. It is estimated that the force drawing the raised portions was canceled by removing the *P. aeruginosa* bacterium from the surface, the warped raised portions recovered their original shape before the *P. aeruginosa* bacterium adhered thereto (the shape extending generally parallel to a normal direction of the synthetic polymer film). Since the tilt (warp) of the raised portions is reset in this way by removing microorganisms, removing microorganisms from the surface of the synthetic polymer film enables recycling of a synthetic polymer film whose surface has a microbicidal effect and/or reactivation of the surface.

The reason why wiping the surface of the synthetic polymer film is an effective way of removing microorganisms from the surface can be estimated as follows.

Although, as previously described, part of a *P. aeruginosa* bacterium resides in the gap between raised portions, the *P. aeruginosa* bacterium mainly adheres to the tip end side of the raised portions as seen from FIG. 5 and FIG. 16. The *P. aeruginosa* bacterium rarely adheres to the basal side of the raised portions (for example, when the raised portions have a conical shape, near the base of the cone). For example, in FIGS. 16(*a*) to 16(*d*), the *P. aeruginosa* bacterium appear to be adhering to a range of about 50 nm to about 150 nm from the tip ends of the raised portions at the height of about 300 nm. That is, the bacterium adheres to a range of about ⅙ to about ½ of the height of the raised portions from the tip ends of the raised portions. It is estimated that, since microorganisms thus mainly adhere to the tip end side of the raised portions, the microorganisms can be effectively removed by wiping the surface of the synthetic polymer film.

One of the reasons why the better way of removing microorganisms from the surface was physically wiping away the microorganisms than chemically treating the microorganisms may be the following. It is estimated that, when a chemical treatment (e.g., immersion in a washing solution) is carried out for removing microorganisms from the surface, the microorganisms, for example, deform so that there is a probability that the microorganisms adhere to the basal side of the raised portions. Therefore, it is estimated that wiping the surface of the synthetic polymer film with a cloth soaked with water without a chemical treatment on the surface of the synthetic polymer film was an effective way of removing the microorganisms from the surface.

For example, the height of the raised portions, the aspect ratio of the raised portions, the shape of the raised portions, and the like, may be appropriately modified such that the microorganisms adhere only to the tip end side of the raised portions. Here, the aspect ratio of the raised portions refers to a ratio of the height of the raised portions to the two-dimensional size of the raised portions. The height of the raised portions refers to a height in a normal direction of the surface of the synthetic polymer film. Also, the material, hardness, etc., of the resin that forms the synthetic polymer film may be appropriately modified such that the raised portions are capable of warping.

Figure 17:
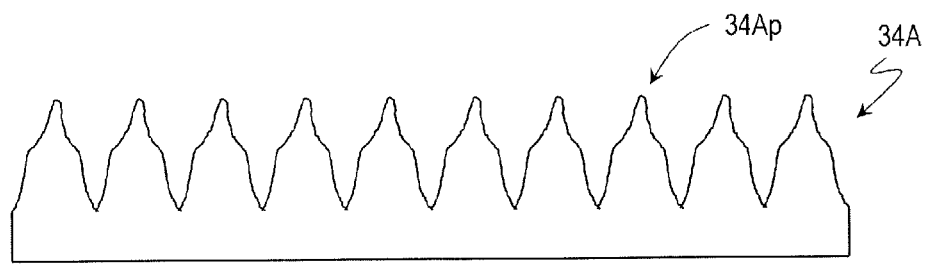
FIG. 17 (a) is an example of a schematic cross-sectional view of a synthetic polymer film 34A. (b) is an enlarged view of (a), showing a schematic cross-sectional view of a raised portion 34Ap. (c) is a SEM image of a cross section of a moth-eye mold used for production of the synthetic polymer film 34A of (a).
Figure 17:
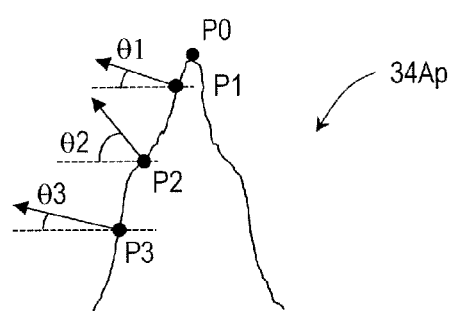
Figure 17:
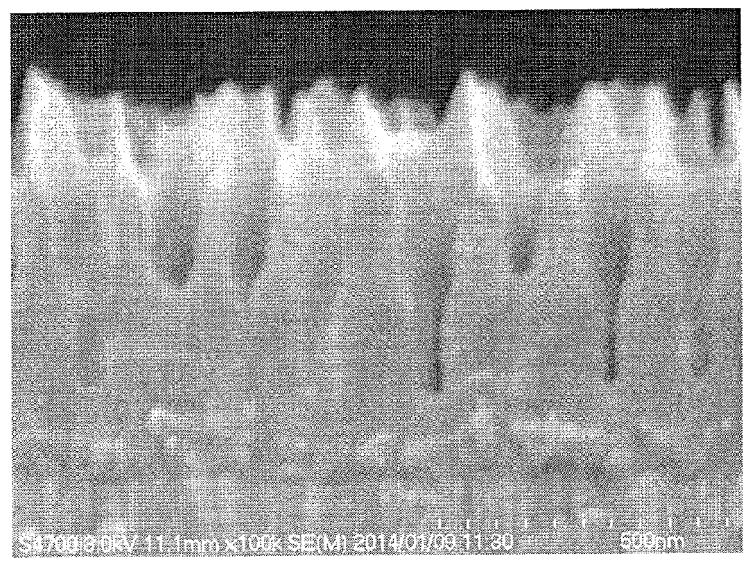

FIG. 17(*a*) is an example of a schematic cross-sectional view of a synthetic polymer film 34A. FIG. 17(*b*) is an enlarged view of FIG. 17(*a*), showing a schematic cross-sectional view of a raised portion 34Ap. FIG. 17(*c*) is a SEM image of a cross section of a moth-eye mold used for production of the synthetic polymer film 34A of FIG. 17(*a*). For example, in a synthetic polymer film which has over its surface raised portions which have a shape such as the raised portions 34Ap shown in FIG. 17(*a*), it is estimated that microorganisms mainly adhere to the tip end side of the raised portions but are unlikely to reach the basal side (bottom side) of the raised portions.

As shown in FIG. 17(*a*), the cross-sectional area of the raised portions 34Ap (the area of a cross section of the raised portions 34Ap which is parallel to the film surface of the synthetic polymer film 34A) increases as the distance from the tip end of the raised portions 34Ap to the cross section (the distance in a normal direction of the synthetic polymer film 34A) increases. The normal to the lateral surface of the raised portions 34Ap of the synthetic polymer film 34A according to an embodiment of the present invention forms an inclination angle with respect to a direction perpendicular to the normal direction of the synthetic polymer film 34A (e.g., a direction parallel to the film surface of the synthetic polymer film 34A). That inclination angle may vary depending on the distance from the tip end of the raised portions 34Ap (the distance in the normal direction of the synthetic polymer film 34A). For example, the inclination angle may vary continuously or discontinuously with respect to the distance from the tip end of the raised portions 34Ap (the distance in the normal direction of the synthetic polymer film 34A).

In FIG. 17(*b*), normal directions at three points P1 to P3 on the lateral surface of the raised portion 34Ap are shown by arrows. Directions perpendicular to the normal directions of the synthetic polymer film 34A (e.g., directions parallel to the film surface of the synthetic polymer film 34A) are shown by broken lines. The inclination angles of the normal lines at the three points P1 to P3 with respect to the directions perpendicular to the normal directions of the synthetic polymer film 34A are designated by θ1 to θ3. The distance from the tip end P0 of the raised portion 34Ap (the distance in a normal direction of the synthetic polymer film 34A) is the smallest at point P1 and the largest at point P3. As shown in FIG. 17(*b*), the inclination angle θ2 at point P2 is greater than the inclination angle θ1 at point P1 at which the distance from the tip end P0 is smaller than at point P2. It is estimated that, when the tip end portion of the raised portion 34Ap has such a configuration that the inclination angle increases as the distance from the tip end of the raised portion 34Ap increases, microorganisms mainly adhere to the tip end side of the raised portion 34Ap and are unlikely to reach the basal side (bottom side) of the raised portion 34Ap. In such a case, it is estimated that wiping away the microorganisms from the surface is easy. The inclination angle θ3 at point P3 may be smaller than the inclination angle θ2 at point P2 at which the distance from the tip end P0 is smaller than at point P3 as shown in FIG. 17(*b*). As a matter of course, the inclination angle θ3 at point P3 may be greater than the inclination angle θ2.

The moth-eye mold configured for production of the synthetic polymer film 34A of FIG. 17(a) has a cross section such as shown in FIG. 17(c). The moth-eye mold shown in FIG. 17(c) is manufactured, for example, through the following manufacture process. The anodization step and the etching step are alternately carried out through multiple cycles, specifically 5 anodization cycles and 4 etching cycles. In the anodization step, the anodization solution used is an oxalic acid aqueous solution (concentration: 0.3 mass %, solution temperature: 10° C.). The anodization is carried out at 80 V for 130 seconds. In the etching step, the etching solution used is a phosphoric acid aqueous solution (10 mass %, 30° C.). The etching is carried out for 25 minutes. Note that, however, the third cycle of the etching step is a half of that duration (12.5 minutes). This causes the inclination of the lateral surfaces of recessed portions of the moth-eye mold to vary in the middle.

Although FIG. 17(a) shows an example of the shape of the raised portions 34Ap of the synthetic polymer film 34A, the raised portions 34Bp of the synthetic polymer film 34B (see FIG. 1(b)) may have a shape such as shown in FIG. 17(a). Conical portions of the raised portions 34Bp may have the shape of the raised portions 34Ap shown in FIG. 17(a).

Synthetic Polymer Film Whose Surface is Treated with Oil

A synthetic polymer film whose surface has a microbicidal effect according to an embodiment of the present invention is applicable to various uses. As previously described, for example, the synthetic polymer film is applicable to uses for sterilization of surfaces of kitchen and bathroom facilities. However, the present invention is not limited to this example. For example, a synthetic polymer film which has a microbicidal surface may be applicable to display panels and touch panels which can be touched by a large number of unspecified users. For example, the synthetic polymer film is applicable to display panels and touch panels placed in hospitals or public places. When applied to such uses, there is a probability that a smear, such as fingerprint, adheres to the synthetic polymer film. When fingerprint adheres to a film (synthetic polymer film) which has the moth-eye structure, removing the fingerprint is difficult even with the use of a washing solution or cloth. For example, there is a probability that the appearance of the display panel or touch panel is marred, or the visibility of information displayed on the display panel or touch panel deteriorates.

Further, as previously described, from the viewpoint of improving the microbicidal effect of the synthetic polymer film, the contact angle with respect to hexadecane is preferably not more than 51°, for example, and the contact angle with respect to hexadecane is preferably small. It is estimated that, in a synthetic polymer film whose contact angle with respect to hexadecane is small, i.e., which has lipophilicity, such a problem frequently arises that fingerprint (finger grease) adhering to the film easily spreads so that the smear is conspicuous.

The present inventors reached the concept of treating the surface of the synthetic polymer film with an oil (providing an oil to the surface) as the way of making a smear adhering to the synthetic polymer film, such as fingerprint, less conspicuous.

A synthetic polymer film according to an embodiment of the present invention is a synthetic polymer film having a surface which has a plurality of raised portions. When viewed in a normal direction of the synthetic polymer film, the two-dimensional size of the plurality of raised portions is in the range of more than 20 nm and less than 500 nm. The surface has a microbicidal effect. The surface is treated with an oil. The surface of any of the synthetic polymer films according to the embodiment of the present invention which have been previously described as examples may be treated with an oil. The surface of the synthetic polymer film according to the embodiment of the present invention is a surface treated with, for example, hexadecane or oleic acid. Here, the oil refers to a liquid which is hardly compatible with water. For example, the oil refers to a liquid which requires 1 L or more of water for solving 1 mL of the liquid.

When a synthetic polymer film according to an embodiment of the present invention has a surface treated with an oil, fingerprint or the like is inconspicuous. When the surface of the synthetic polymer film is not treated with an oil, fingerprint adhering to the surface is conspicuous for the following reasons. When fingerprint (i.e., grease from hands) adheres to a certain portion, the refractive index is different between the portion to which the fingerprint is adhering and the other portions. In addition, the thickness of the fingerprint adhering to that portion is generally large as compared with the height of the raised portions. The appearance of an image viewed through the synthetic polymer film varies so that the portion to which the fingerprint is adhering is conspicuous. On the other hand, in a synthetic polymer film whose surface is treated with an oil, the surface is provided with an oil beforehand. Therefore, even if grease from hands adheres to the surface, the difference in refractive index rarely occurs. (For example, the refractive index of hexadecane is about 1.43, and the refractive index of oleic acid is about 1.46.) Further, the grease from hands is solved with the oil and spreads so that the difference in refractive index from the surroundings and/or the difference in thickness from the surroundings decreases. For these reasons, the fingerprint is inconspicuous. Even when fingerprint adheres to a panel by touching the panel with fingers or the like, deterioration of the appearance of the panel or deterioration of the visibility of information displayed on the panel, for example, can be suppressed. Further, since the surface is provided with an oil beforehand, fingerprint adhering to the surface can be easily wiped away.

As will be described below with experimental examples, it was verified that a synthetic polymer film whose surface is provided with an oil also has a microbicidal effect.

Sample films No. 14 to No. 18 shown in Table 6 below were evaluated as to the microbicidal ability against *P. aeruginosa* bacteria.

Sample films No. 14 to No. 17 were produced using the acrylic resin E to which a silicone lubricant was added (the same acrylic resin as that used for sample film No. 12) with the use of the same mold as that described above.

In sample film No. 14, 10 μL oleic acid (high grade oleic acid manufactured by Hayashi Pure Chemical Ind., Ltd.) was provided to the surface. Thereafter, the film was rubbed with BEMCOT (registered trademark, product name: BEMCOT CT-8, manufactured by Asahi Kasei Corp.) in the up and down direction and in the left and right direction, 10 times for each direction, such that the oleic acid was uniformly provided across the film, whereby sample film No. 14 was obtained.

Sample film No. 15 is different from sample film No. 14 in that hexadecane was provided to the surface instead of oleic acid.

In sample film No. 16, the surface was provided with fingerprint. The grease of the forehead was scraped by a finger and placed on the surface of the film 12 times (in the form of 3 rows and 4 columns). Thereafter, the grease was spread uniformly across the film in the same way as in sample film No. 14.

The surface of sample film No. 17 was provided with nothing.

Sample film No. 18 was a PET film which was used as the base film of sample films No. 14 to No. 17.

The microbicidal ability against *P. aeruginosa* bacteria was evaluated through the following procedure:

1. Bacterial dilution A2 was prepared in the same way as the bacterial dilution A that has been previously described for Table 1. The bacterial dilution A2 was different from the bacterial dilution A in that the bacteria count of *P. aeruginosa* bacteria was on the order of 1E+05 CFU/mL. The bacteria count of *P. aeruginosa* bacteria in the bacterial dilution A2 was 3.9E+05 CFU/mL in sample films No. 14 and No. 16 to No. 18 and was 2.9+05 CFU/mL in sample film No. 15;

2. A 400 μL drop of the bacterial dilution A2 was placed on each of the sample films, and a cover (e.g., cover glass) was placed over the bacterial dilution A2 to adjust the amount of the bacterial dilution A2 per unit area (about 0.4 mL/cm$^2$);

3. The samples were left in an environment where the temperature was 35° C. and the relative humidity was 100% for a predetermined time period (the time period: 0 hour (5 minutes), 4 hours, 24 hours, 72 hours);

4. The entire sample film with the bacterial dilution A2 and 9.6 mL sterilized water were put into a filter bag. The sample films were rubbed with hands over the filter bag to sufficiently wash away the bacteria from the sample films. The post-wash solution in the filter bag (bacterial dilution B2) was a 25-fold dilution of the bacterial dilution A2.

5. The bacterial dilution B2 was diluted 10-fold with sterilized water, whereby bacterial dilution C2 was prepared. Specifically, the bacterial dilution C2 was prepared by putting 120 μL bacterial dilution B2 into 1.08 mL sterilized water.

6. The bacterial dilution C2 was diluted 10-fold in the same way as preparation of the bacterial dilution C2, whereby bacterial dilution D2 was prepared. Further, the bacterial dilution D2 was diluted 10-fold, whereby bacterial dilution E2 was prepared.

7. 1 mL drops of the bacterial dilutions B2, C2, D2 and E2 were placed on Petrifilm™ media (product name: Aerobic Count Plate (AC), manufactured by 3M). The bacteria were cultured at 35° C. with the relative humidity of 100%. After 48 hours, the number of bacteria in the bacterial dilution B2 was counted.

Note that, although in 5.6 h) of JIS 22801 a phosphate-buffered saline is used in preparation of a diluted solution, sterilized water is sometimes used in this specification. When sterilized water is used, there is a probability that the difference in osmotic pressure between the solution in the cells of microorganism and the sterilized water, rather than the raised portions provided over the surface of the sample films, will be a cause of death of microorganisms. As for this probability, it was verified that bacteria did not die on a PET film which did not have raised portions over the surface (e.g., sample films No. 13 and No. 18). It was verified that the microbicidal effect of the raised portions provided over the surface of the sample films can be examined even when sterilized water is used.

Figure 18:
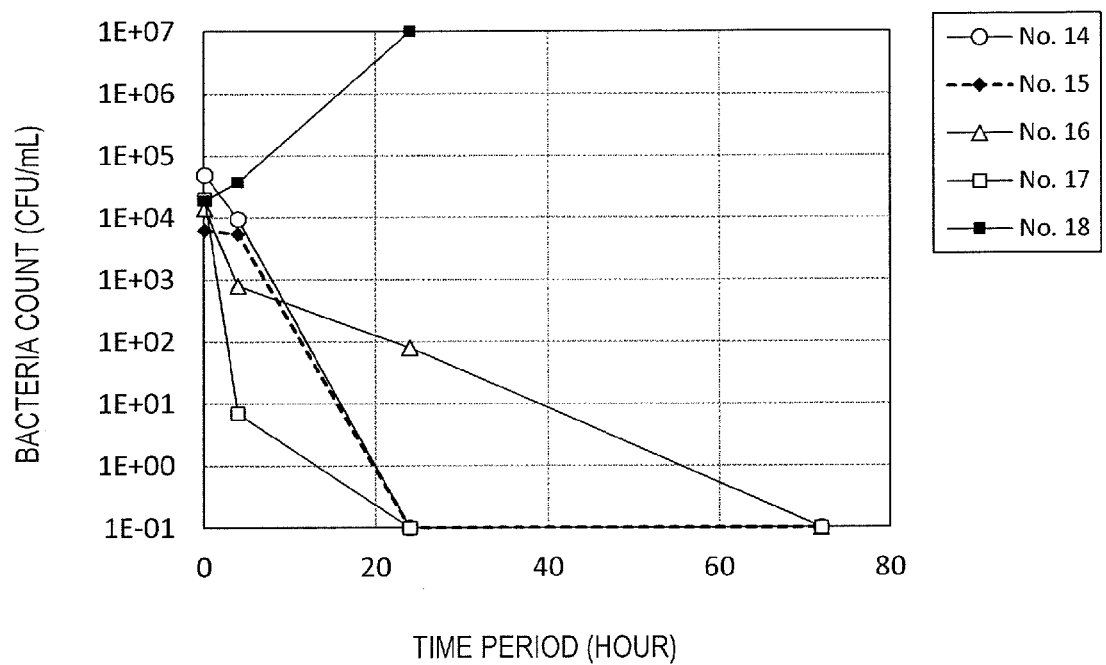
FIG. 18 A graph showing the results of evaluation of the microbicidal ability of the sample films. The horizontal axis represents the time period that the sample film was left (hour). The vertical axis represents the bacteria count (CFU/mL).

The results are shown in FIG. 18. FIG. 18 is a graph showing the results of evaluation of the microbicidal ability of sample films No. 14 to No. 18. The horizontal axis represents the time period (hour). The vertical axis represents the bacteria count (CFU/mL) in the bacterial dilution B2. Note that, in FIG. 18, when the bacteria count is 0, it is plotted as 0.1 for the sake of visibility.

As clearly seen from FIG. 18, every one of sample films No. 14 to No. 17 had microbicidal ability. Sample film No. 18 (PET) did not have microbicidal ability. It was found that the bacteria count increased to such a level that it was uncountable after passage of the time period of 24 hours. It was found from the results of sample films No. 14 to No. 16 that a synthetic polymer film whose surface was provided with an oil had a microbicidal effect. Particularly, sample film No. 14 whose surface was provided with oleic acid and sample film No. 15 whose surface was provided with hexadecane had excellent microbicidal effects, which were hardly inferior to that of sample film No. 17 whose surface was not provided with an oil. In the case of sample film No. 16 with fingerprint on the surface, the time consumed before the bacteria count reached 0 was long as compared with sample film No. 17 whose surface was not provided with an oil, but sample film No. 16 still had a microbicidal effect.

TABLE 6

| No. | SYNTHETIC POLYMER FILM (BASE FILM: PET) | MICRO-BICIDAL ABILITY |
|---|---|---|
| 14 | ACRYLIC RESIN E WITH SILICONE LUBRICANT ADDED + OLEIC ACID | ◯ |
| 15 | ACRYLIC RESIN E WITH SILICONE LUBRICANT ADDED + HEXADECANE | ◯ |
| 16 | ACRYLIC RESIN E WITH SILICONE LUBRICANT ADDED + FINGERPRINT | ◯ |
| 17 | ACRYLIC RESIN E WITH SILICONE LUBRICANT ADDED | ◯ |
| 18 | PET | X |

Figure 19:
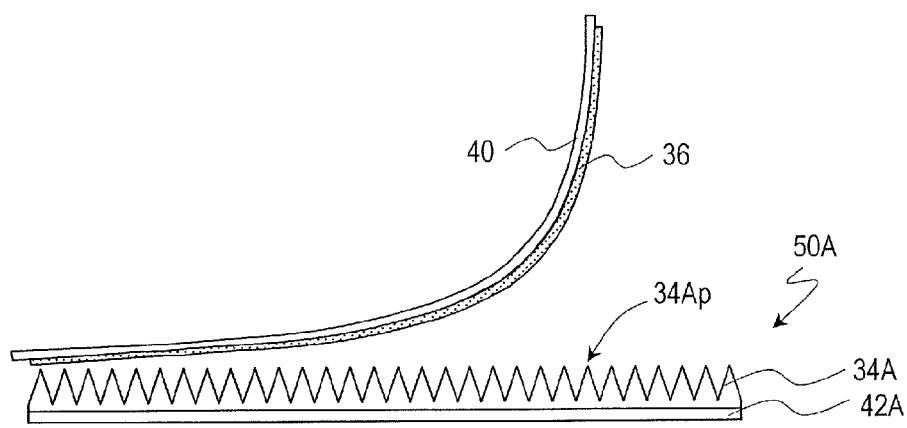
FIG. 19 (a) to (c) are schematic cross-sectional views for illustrating an example of a production method of a synthetic polymer film whose surface is treated with an oil.
Figure 19:
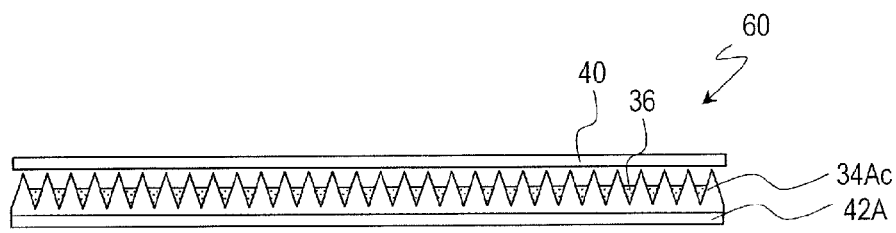
Figure 19:
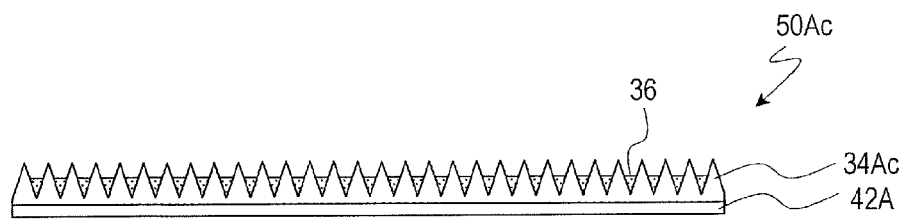

A production method of a synthetic polymer film 34Ac whose surface is treated with an oil is described with reference to FIGS. 19(*a*) to 19(*c*). FIGS. 19(*a*) to 19(*c*) are schematic cross-sectional views for illustrating an example of a production method of a synthetic polymer film 34Ac whose surface is treated with an oil.

A production method of the synthetic polymer film 34Ac whose surface has a microbicidal effect according to an embodiment of the present invention includes the steps of: (a) providing a synthetic polymer film 34A having a surface which has a plurality of raised portions 34Ap, a two-dimensional size of the plurality of raised portions 34Ap being in a range of more than 20 nm and less than 500 nm when viewed in a normal direction of the synthetic polymer film 34A, the surface having a microbicidal effect; (b) providing a cover film 40 whose surface is provided with an oil 36; (c) bringing the plurality of raised portions 34Ap and the oil 36 into contact with each other while the synthetic polymer film 34A and the cover film 40 oppose each other; and (d) separating the cover film 40 from the synthetic polymer film 34Ac.

First, as shown in FIG. 19(*a*), a synthetic polymer film 34A that has a plurality of raised portions 34Ap and a cover film 40 whose surface is provided with an oil 36 are provided. A film 50A may be provided which includes a base film 42A and a synthetic polymer film 34A formed on the base film 42A. The cover film 40 can be made of, for example, the same material as that of the base film 42A. The thickness of the oil 36 is, for example, from 1 μm to several tens of micrometers.

Then, as shown in FIG. 19(b), the synthetic polymer film 34A and the cover film 40 are bound together. The plurality of raised portions 34Ap and the oil 36 are brought into contact with each other while the synthetic polymer film 34A and the cover film 40 oppose each other. A multilayer structure 60 consisting of the synthetic polymer film 34A and the cover film 40 is formed. In the multilayer structure 60, the oil 36 on the surface of the cover film 40 is provided to the surface of the synthetic polymer film 34A, whereby a synthetic polymer film 34Ac whose surface is treated with the oil 36 is formed.

The multilayer structure 60 includes: a synthetic polymer film 34A having a surface which has a plurality of raised portions 34Ap, a two-dimensional size of the plurality of raised portions 34Ap being in a range of more than 20 nm and less than 500 nm when viewed in a normal direction of the synthetic polymer film 34A, the surface having a microbicidal effect; and a cover film 40 whose surface is provided with an oil 36. The cover film 40 is arranged such that the oil 36 is in contact with the plurality of raised portions 34Ap. The cover film 40 may be arranged, for example, generally parallel to the synthetic polymer film 34A.

Then, as shown in FIG. 19(c), the cover film 40 is separated from the synthetic polymer film 34Ac. The resultant synthetic polymer film 34Ac has a surface treated with the oil 36. When the film 50A which has the base film 42A is provided, a film 50Ac can be formed which includes a base film 42A and a synthetic polymer film 34Ac whose surface lying on the base film 42A is treated with the oil 36.

As shown in FIGS. 19(b) and 19(c), the surface of the oil 36 is, for example, generally parallel to the film surface of the synthetic polymer film 34A. As shown in FIGS. 19(b) and 19(c), for example, the tip end portions of the plurality of raised portions 34Ap protrude above the surface of the oil 36. However, the present invention is not limited to this example. The oil 36 may generally entirely cover the plurality of raised portions 34Ap. Note that, however, the distance from the oil surface to the tip ends of the plurality of raised portions 34Ap (the distance in a normal direction of the synthetic polymer film 34A) is, for example, not more than 10 μm. Since the size of bacteria is, for example, from several hundreds of nanometers to about 5 μm, the distance from the oil surface to the tip ends of the plurality of raised portions 34Ap is preferably not more than several micrometers, for example. The distance from the oil surface to the tip ends of the plurality of raised portions 34Ap may be less than 1 μm. The surface of the oil 36 may be generally parallel to the surface of the plurality of raised portions 34Ap. That is, the surface of the oil 36 may vary according to the shape of the raised portions 34Ap. Note that, however, in this case also, as previously described, the distance from the oil surface to the tip ends of the plurality of raised portions 34Ap (the distance in a normal direction of the synthetic polymer film 34A) is, for example, not more than 10 μm. Since the size of bacteria is, for example, from several hundreds of nanometers to about 5 μm, the distance from the oil surface to the tip ends of the plurality of raised portions 34Ap is preferably not more than several micrometers, for example. The distance from the oil surface to the tip ends of the plurality of raised portions 34Ap may be less than 1 μm.

According to the above-described production method, a synthetic polymer film whose surface is treated with an oil can be readily produced from a synthetic polymer film produced by the production method that is based on the roll-to-roll method which has been described with reference to FIG. 3. The synthetic polymer film produced by the production method of FIG. 3 is wound up by a winding roller. This synthetic polymer film is appropriately fed from the roll for formation of a synthetic polymer film whose surface is treated with an oil by the production method of FIG. 19.

The multilayer structure 60 itself may be, for example, shipped, distributed, or sold. For example, the cover film 40 may be separated from the synthetic polymer film 34Ac immediately before using the synthetic polymer film 34Ac. The surface of the synthetic polymer film 34Ac can be sufficiently protected until immediately before the start of use.

A method for producing the synthetic polymer film 34Ac whose surface is treated with an oil from the synthetic polymer film 34A has been described with reference to FIG. 19. A synthetic polymer film whose surface is treated with an oil may be produced from the synthetic polymer film 34B (see FIG. 1(b)) using the same method.

INDUSTRIAL APPLICABILITY

A synthetic polymer film which has a bactericidal surface according to an embodiment of the present invention is applicable to various uses including, for example, uses for sterilization of surfaces of kitchen and bathroom facilities. The synthetic polymer film which has a bactericidal surface according to an embodiment of the present invention can be produced at low cost.

REFERENCE SIGNS LIST 34A, 34B, 34Ac synthetic polymer film
34Ap, 34Bp raised portion
42A, 42B base film
50A, 50B, 50Ac film
100, 100A, 100B moth-eye mold

The invention claimed is:

1. A method for reactivating a surface of a synthetic polymer film, comprising the steps of:
   (a) providing a synthetic polymer film comprising a surface which has a plurality of first raised portions, wherein a two-dimensional size of the plurality of first raised portions is in a range of more than 20 nm and less than 500 nm when viewed in a normal direction of the synthetic polymer film, and the surface has a microbicidal effect, the synthetic polymer film having a microorganism adhering to the surface; and
   (b) removing the microorganism by wiping the surface with a cloth soaked with water or alcohol;
   wherein the synthetic polymer film further comprises a plurality of second raised portions superimposedly formed over the plurality of first raised portions, and a two-dimensional size of the plurality of second raised portions is smaller than the two-dimensional size of the plurality of first raised portions and does not exceed 100 nm.

2. The method of claim 1, wherein a static contact angle of the surface with respect to hexadecane is not more than 31°.

3. The method of claim 1, wherein a static contact angle of the surface with respect to water is not more than 133°.

4. The method of claim 1, wherein an adjoining distance of the plurality of first raised portions is more than 20 nm and not more than 1000 nm.

5. The method of claim 1, wherein a height of the plurality of first raised portions is not less than 50 nm and less than 500 nm.

6. The method of claim 1, wherein the plurality of first raised portions are capable of warping when coming in contact with a microorganism.

7. The method of claim 1, wherein a normal to a lateral surface of the plurality of first raised portions forms an inclination angle with respect to a direction perpendicular to the normal direction of the synthetic polymer film, and the inclination angle varies continuously or discontinuously with respect to a distance from a tip end of the plurality of first raised portions in the normal direction of the synthetic polymer film.

8. The method of claim 1, wherein the plurality of second raised portions include a generally conical portion.

9. The method of claim 1, wherein a height of the plurality of second raised portions is more than 20 nm and not more than 100 nm.

10. The method of claim 1, wherein the synthetic polymer film further comprises a lubricant.

11. The method of claim 10, wherein a HLB value of the lubricant is less than 7.

12. The method of claim 1, wherein the surface is treated with a mold releasing agent.

13. The method of claim 1, wherein the surface is treated with an oil.

* * * * *